United States Patent
Silverman

(10) Patent No.: US 6,391,014 B1
(45) Date of Patent: *May 21, 2002

(54) STRONG DIAPHRAGM/SAFE NEEDLE/ CONVERTING DEVICE COMBINATIONS AND THEIR INDIVIDUAL COMPONENTS

(76) Inventor: David G. Silverman, 3 Meeker Hill Rd., Redding, CT (US) 06896

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/994,718

(22) Filed: Dec. 19, 1997

Related U.S. Application Data

(60) Provisional application No. 60/033,720, filed on Dec. 20, 1996.

(51) Int. Cl.[7] ............................................... A61B 19/00
(52) U.S. Cl. ........................ 604/415; 604/411; 604/239; 604/272; 604/274
(58) Field of Search ............................ 604/403, 411, 604/415, 86, 200, 201, 272, 273, 239, 237, 274; 128/898

(56) References Cited

U.S. PATENT DOCUMENTS

| | | | |
|---|---|---|---|
| 2,906,423 A | * | 9/1959 | Sandhage |
| 3,492,992 A | * | 2/1970 | Kurtz |
| 3,509,880 A | * | 5/1970 | Guttman |
| 3,653,528 A | * | 4/1972 | Wimmer ...................... 215/247 |
| 4,190,048 A | * | 2/1980 | Sampson ..................... 604/175 |
| 4,197,848 A | * | 4/1980 | Garrett et al. ................. 604/19 |
| 4,411,657 A | * | 10/1983 | Galindo |
| 4,413,993 A | * | 11/1983 | Guttman |
| 5,060,812 A | * | 10/1991 | Ogle, II ....................... 215/247 |
| 5,188,620 A | * | 2/1993 | Jepson et al. ................ 604/283 |
| 5,211,638 A | * | 5/1993 | Dudar et al. ................. 604/283 |
| 5,242,393 A | * | 9/1993 | Brimhall et al. ............... 604/86 |
| 5,328,041 A | * | 7/1994 | Hook et al. ................... 215/247 |
| 5,403,293 A | * | 4/1995 | Grabenkort .................. 604/256 |
| 5,403,525 A | * | 4/1995 | Helgren et al. .............. 264/443 |
| 5,411,499 A | * | 5/1995 | Dudar et al. ................. 604/411 |
| 5,478,328 A | * | 12/1995 | Silverman et al. ........... 604/272 |
| 5,569,213 A | * | 10/1996 | Humphrey ................... 604/239 |

* cited by examiner

Primary Examiner—Brian L. Casler
Assistant Examiner—Jeremy Thissell
(74) Attorney, Agent, or Firm—Ostrolenk, Faber, Gerb & Soffen, LLP

(57) ABSTRACT

A device that converts a diaphragm prior to its first penetration for clinical use, to be more readily penetrable by a needle or cannula after conversion, by creating a prehole or preslit in the surface of the diaphragm.

59 Claims, 32 Drawing Sheets

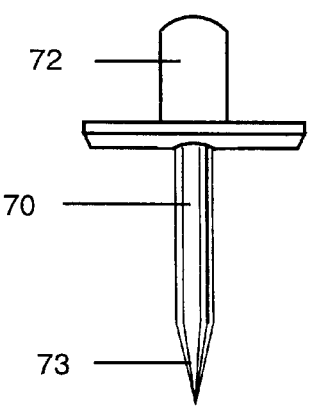
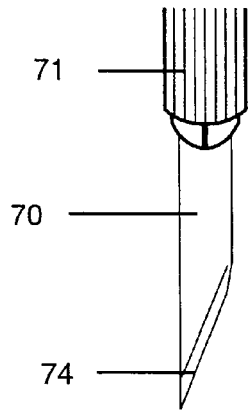
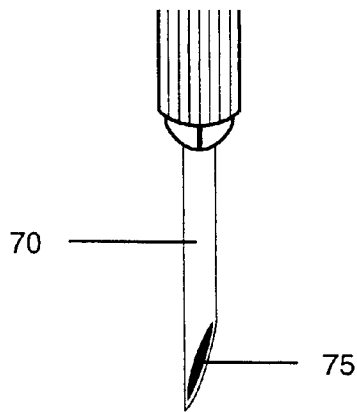
fig. 14a fig. 14b fig. 14c
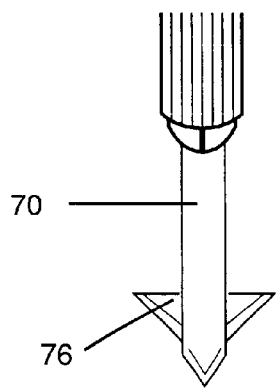
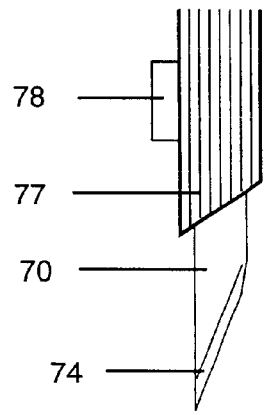
fig. 14d fig. 14e

140

6

140

141

STRONG DIAPHRAGM/SAFE NEEDLE/ CONVERTING DEVICE COMBINATIONS AND THEIR INDIVIDUAL COMPONENTS

CROSS-REFERENCE TO RELATED APPLICATIONS

This application is based on U.S. Provisional Application No. 60/033,720 filed Dec. 20, 1996, incorporated by reference.

It is related to the applicants' prior U.S. Pat. No. 5,478, 328 issued Dec. 26, 1995, incorporated by reference.

It is also related to the applicants' other applications, incorporated by reference, filed on even date herewith, namely, a three-part series of disclosures titled:

I="Strong Diaphragm/Safe Needle Units and Components for Transfer of Fluids";

II="Strong Diaphragm/Safe Needle/Converting Device Combinations and Their Individual Components"; and III="Reversibly Compressed Prechannelled/Preweakened Diaphragms for Use with Blunt Cannulae and Safe Needles".

BACKGROUND OF THE INVENTION

The present series of inventions was prompted by the need to decrease the exposure of healthcare workers to potentially harmful needle sticks which, as detailed in the inventors' recent disclosure (U.S. Pat. No. 5,478,328 in 1995), pose the risk of infection with diseases such as hepatitis and AIDS. All too commonly, inadvertent needle sticks occur with needles that are being used for, or have been used for, penetrating a diaphragm. The varied uses of such needle/diaphragm combinations include: (a) withdrawing from or injecting into a medication vial, collection tube, or fluid bag; (b) injecting or withdrawing medications or fluids via tubing attached to an intravenous catheter.

The common features of the present series of inventions include needle/diaphragm combinations wherein:

(a) "safe yet penetrating" needles, such as those illustrated, in part, in our prior patent (U.S. Pat. No. 5,478,328) and claimed herein, are designed to provide a compromise between "penetrating but dangerous" sharp needles of traditional systems and newer "safe but nonpenetrating" blunt cannulae of needleless blunt-cannula systems (described below). The inventive needles are designed to decrease the likelihood of harmful puncture of the skin of a healthcare worker (compared to that associated with a traditional needle) by one or both of the following:

1) lessening the pointedness of the tip;
2) providing one or more recessed orifices as opposed to an open tip;

(b) the "strong yet penetrable" diaphragms of the present disclosures are a compromise between the "strong but (relatively) impenetrable" and the "penetrable but weak" extremes described in the prior art (described below). They are designed to:

1) provide an intact covering or plug with a section that, at the time of clinical use, can be pierced with greater penetrability than a conventional diaphragm (which requires penetration by a traditional "penetrating but dangerous" sharp-tip needle);
2) have the integrity and long-term shelf-life approximate to that of a conventional diaphragm and thus maintain the sterility of the enclosed contents for months or years prior to the first clinical usage of the needle/ diaphragm combination;
3) have the versatility of a conventional diaphragm (i.e., be able to cover openings with a wide range of diameters as may be found on injection ports, bottle tops, etc.);
4) provide a snug, secure fit for the needle or cannula which pierces it and thereby prevent leakage and dislodgement;
5) provide resealing properties after needle or cannula removal that enable the diaphragm to maintain its integrity and hence the sterility of the underlying contents for a satisfactory duration.

In addition, Disclosure #II of the three-part series introduces the concept of and means of a "converting" mechanism for modifying the diaphragm immediately prior to its first penetration for clinical use. This converts a strong diaphragm which otherwise would not be so readily penetrable by a given "safe" needle or cannula to a diaphragm which can be used in combination with said needle or cannula. The conversion may be accomplished by utilizing a device to puncture and/or slit the diaphragm (herein called a "convertor").

In addition, Disclosure #III of the three-part series introduces the concept of and means of providing reversible compression of a prechannelled or preweakened diaphragm. This enables one to ensure effective closure of a preslit or preweakened region before a diaphragm has been penetrated by a needle or cannula and, in many embodiments, restoration of the ancillary pressure may secure effective closure even after penetration.

As alluded to above, prior to the present invention, two extremes of needle/diaphragm combinations have been available: 1) Strong Diaphragm/ Dangerous Needle; or 2) Weak Diaphragm/Safe Cannula. These are described below:

1. Strong Diaphragm/Dangerous Needle—It traditionally was felt that, in virtually all settings, needle insertion through a diaphragm necessitated the use of a sharp needle. Known hypodermic needles for use with penetrating diaphragms typically have:
   (a) a sharp point;
   (b) an open tip.

Such needles have cutting points, formed by a beveled cut typically at an angle of approximately 45° (or less) to the longitudinal axis of the needle shaft with an opening created at the junction of the beveled edge and the needle bore. Unfortunately, these features pose a threat to anyone who comes into contact with a used needle. The sharp point increases the likelihood of skin puncture; as evidenced by the large number of injuries, relatively little force is needed to penetrate the skin during an inadvertent stick with a sharp needle. The open tip can house infected fluid or tissue (herein called an inoculum); this increases the likelihood that a needle stick will result in disease transmission. The sharp-point, open-tip construction not only increases the risk of injury to a healthcare worker during usage but also increases the likelihood of accidental injury during recapping as a consequence of missing the cap or actually piercing the side of the cap.

2) Weak Diaphragm/Safe Cannula—The newly designed "needleless" blunt-cannula systems (e.g., the InterLink System, Baxter Healthcare Corp., Deerfield Ill. in collaboration with Becton-Dickinson Co., Franklin Lakes N.J.; and the Lifeshields system, Abbott Laboratories, Abbott Park Ill.) contain a diaphragm that is modified at the time of manufacture to such a degree that it is penetrable by an "absolutely" blunt-tipped cannula (with an end that typically is flat or hemispherical, and never with less than a 75° angle to the longitudinal axis of the cannula shaft). The manufacture of the diaphragm (herein called a "blunt-cannula diaphragm") has been taught within the prior decade as follows:

(a) cutting a slit into the central portion of the diaphragm with a knife ("preslitting") (Jepson, Dudaran, and Finley WO89/06553 & WO90/11108 in 1989/90—Baxter).

(b) reinforcing such a preslit diaphragm by covering the main plug with a thin diaphragm portion and using a metal ferrule which remains permanently in place for securing the inner and outer members of the stopper assembly together (Hook U.S. Pat. No. 5,328,041 in 1994—Abbott). In justifying the need for his more complex process (which includes two stopper members and a ferrule), the inventor stated that this was required to maintain sterility of the contents of vials covered with a preslit diaphragm: "the same prepierced construction used in prepierced reseals cannot be implemented for the stoppers on vials because of sterility and shelf-life degradation questions."

(c) molding the diaphragm in two pieces which are joined by a penetrable hinged region (Grabenkort U.S. Pat. No. 5,403,293 in 1995—Abbott). Although Grabenkort claimed that his method of "compression molding allows the tolerances at the hinged region to be better controlled than the alternate method of cutting a slit into a rubber diaphragm (as originally described in a patent assigned to Baxter), the procedure to accomplish this appears to be more complicated as it involves the production of a stiff annular collar having a first and second annular flange.

(d) using ultrasonic heating to create a weakened portion that extends at least partially through the diaphragm's midsection. The horn and anvil of the mounting device conduct heat away from the outer surfaces, thereby allowing them to remain continuous and unbroken (Helgren U.S. Pat. No 5,403,525 in 1995—Abbott).

Review of the earlier prior art shows that the use of a more readily penetrable diaphragm was taught 30 years previously, but none of the inventions of the prior art was designed to facilitate passage of a "safe" needle as described in the present invention. Wimmer (U.S. Pat. No. 3,653,528) taught a means of creating an indentation in the outer surface to facilitate piercing without coring by a standard hypodermic needle. Sandhage (U.S. Pat. No. 2,906,423 in 1959) described a preslit diaphragm which was puncturable by a round-tip plastic "needle" which was so blunt that it was also able to be inserted into the teat of a cow to inject medication for the treatment of mastitis; however, this required lubricant to "fill up the cut slit" after needle entry "to aid in preventing the entry of contaminant organisms." Ogle (U.S. Pat. No. 5,060,812) described diaphragms which were modified to such a degree that they were penetrable by a syringe tip or nozzle (as opposed to a needle or cannula). Garrett (U.S. Pat. No. 4,197,848 in 1980) described a resilient, impermeable membrane for a urinary irrigation system, wherein said membrane had a normally closed, resiliently deformable slit. Said slit was maintained closed by compression, but was penetrable by the blunt end of a syringe. Baxter, the assignee of that invention, noted in a subsequent disclosure (WO 90/11103) that there was still a need for a preslit injection site which "will reliably reseal . . . ."

Although the blunt-cannula diaphragms of the Baxter and Abbott needleless systems tend to self-seal after blunt cannula insertion, they do not guarantee adequate shelf-life and sterility in all contexts:

a) Because they require an appreciable degree of prechannelling or weakening at the time of manufacture, they have not been recommended for prolonged drug storage even prior to first clinical use and especially after they have been penetrated by a needle or cannula. Even in the prior art configuration in which the preslit extends only partway through the blunt-cannula diaphragm, "the end of the blunt cannula will be used to tear through the remainder of the sealing member." (WO 90/11103) This necessitates a very weak "tearable" portion which may restrict shelf-life, and it leads to the potential for poor resealing as a result of the tearing process. This has led to modifications such as the two stopper members and ferrule described above (Hooks U.S. Pat. No. 5,328,041) or an extra valve which serves to reinforce the potentially incompetent site of needle/cannula entry and thereby reduce the risk of leakage (Brimhall U.S. Pat. No. 5,242,393). Despite these modifications, bottles and bags that either house or transfer medication and/or fluids for extended periods of time typically are not equipped for use with the Baxter or Abbott blunt-cannula systems.

b) It is recommended that such blunt-cannula diaphragms be used only with specially designed blunt cannulae since they are prone to damage by sharp needles. Said cannulae have been described as having distal ends which are completely blunt (90° degree angle to the longitudinal axis), arcuate, or hemispherical or as having a lead post which extends beyond the end of the cannula (to guide insertion) or a taper with at least a 75° angle to the longitudinal axis. Greater tapers and actual points were avoided in large part because of the preslit/ preweakened diaphragm's susceptibility to damage. The inventors of needleless systems also proposed the use of conventional lubricant "to further reduce the friction and lower the insertion force required." (WO 90/11103)

c) The blunt-cannula diaphragms only can accept blunt cannulae of limited diameter and the diaphragm itself cannot be provided in the widths required to cover variously sized bottle tops, injection ports, and collection tubes without unacceptably compromising diaphragm integrity. As stated by the inventors (WO 90/11103) of the blunt-cannula system: "To provide for leak-free insertion, the length of the slit in the sealing member must be less than one-half the circumference of the cannula being inserted therethrough [—as a consequence of the greater penetrating ability of our inventive needles, the length of the slit would not so severely limit the diameter of the fluid channel when the proposed inventive needles are used] . . . . In addition, the slit length must be great enough, given the elastic limit of the sealing member, to prevent tearing during insertion." [—again, this should be less of a problem when a more tapered device (e.g., inventive needle) is used].

d) In order to accommodate a blunt cannula, the preslit typically extends to the surface or an indentation is produced so as to facilitate blunt cannula insertion. Either of these surface modifications may limit the effectiveness of antiseptic swabbing. Attempts to overcome this problem have entailed the addition of a potentially costly step in the manufacturing process, including covering the preslit stopper with a second member (which is to be torn by the blunt cannula).

The absolutely blunt cannulae of the Baxter and Abbott needleless systems also pose limitations. As stated above, they can be of only limited diameter (and thus can allow only limited flow rates) as they would otherwise require an unacceptably large slit in the diaphragm to allow insertion of their blunt tip. In addition, they tend to slip out of the blunt-cannula diaphragm, a problem that could be partially mitigated by increasing cannula length, but such a change would slow flow even further. Realizing the potential problems associated with a standard blunt cannula system, the inventors (WO 90/11103) note: "In accordance with further aspects of this invention, the blunt cannula may be provided with features that facilitate insertion into the injection site, enhance fluid flow or dispersion, increase tug resistance, and reduce kickback." These include: 1) the inclusion of a plurality of elongate discharge slits to improve flow which otherwise may be compromised by the cannula's narrow diameter as well as to decrease the contact surface area so as to facilitate insertion; 2) grooves on the side of the cannula to reduce surface area; 3) a lead post to guide cannula insertion; 4) annular barbs to reduce kickback; 5) matching locking means, gripping means, and "retaining fingers" to secure engagement. Moreover, the use of blunt cannulae necessitates modification or replacement of existing setups, so that a blunt-cannula diaphragm is always available. The use of the prior art blunt cannula in the absence of a setup with a preslit or weakened diaphragm is virtually impossible unless one inserts a special "spike" adaptor. One side of the adaptor has a sharply pointed, open-tipped spike which can pierce a standard diaphragm; the other side has a preslit diaphragm. The spike must remain in place as long as the blunt cannula is used; and it must be discarded as a potentially hazardous sharp object (akin to a "penetrating but dangerous" needle) once it is no longer required. To the best of our knowledge, there has been no attempt to increase cannula penetrating properties in a manner comparable to that of the present disclosure; i.e., there has been no attempt to increase penetrating capabilities by using a tapered needle (such as those claimed in the present three-part series) and thereby allowing for an inherently stronger entry point in the diaphragm.

The limitations of needleless systems are significant to the degree that the New York State Study on Needlestick Prevention Devices (in 1992) reported that two-thirds of healthcare workers felt that special training in the use of a needleless device was required and 20.3% of the workers at a major test center believed delivery was impeded with the device. Furthermore, the report noted that, because of the inability to provide blunt-cannula diaphragms for most containers (e.g. bottles, bags), ". . . needles used with the system continued to be a hazard for injury. In one institution, needles continued to be used for administering heparin or saline 'flushes' while in the other hospital, in an attempt to avoid this hazard, a complicated system using multiple components was put into place." These factors led the compilers of the NYS report to conclude that blunt-cannula systems are less cost-effective than systems using traditional sharp, open-tipped needles enclosed in a plastic shield; thus, although they do not eliminate the potential to contact a dangerous needle, the report concluded that shielded needle systems produce "greater reductions in needlestick injuries" than the needleless systems. Of note, neither the NYS Study nor an Apr. 16, 1992 FDA Safety Alert ("Needlestick and other risks from hypodermic needles on secondary i.v. administration sets") recommended or even mentioned the use of an intrinsically safer needle (as opposed to a "safe but nonpenetrating" blunt cannula or a "penetrating but dangerous" sharp needle which is extrinsically modified with a shield). This provides strong evidence that the subject matter disclosed herein, and in the applications and patents incorporated by reference, was not apparent even to experts and leaders in this field.

SUMMARY OF THE INVENTION

The present disclosure is #II of a three-part series of disclosures describing "Strong Diaphragm/Safe Needle" systems and the design and use of their individual components in order to bridge the gap between the Strong Diaphragm/Dangerous Needle and Weak Diaphragm/Safe Cannula extremes of the prior art. An important advantage of the present inventions is that, in contrast to the prior art, they provide healthcare worker safety while maintaining diaphragm integrity; i.e., the inventive series of needles and diaphragms avoid the need for diaphragms which are compromised to the point of having suboptimal sealing and unacceptably short shelf-lives as well as avoiding the need for sharp, open-tipped hypodermic needles or spike adaptors that pose infectious risks to healthcare workers. In most embodiments of the present disclosure, needle configurations which have not previously been recommended for diaphragm penetration (except for the suggestion of such in the inventors' original patent, U.S. Pat. No. 5,478,328 in 1995) are employed. They pose far less risk to healthcare workers than standard hypodermic needles and can be matched with diaphragms to optimize needle/diaphragm efficiency and versatility.

The present disclosure focuses on a design process that entails the introduction of an optional additional step at the time of initial usage: the diaphragm is designed such that it can remain wholly or substantially intact until it is punctured or slit with a "convertor" just prior to use with a specially matched blunt-tip, partially blunt-tip, and/or recessed-orifice "safe" needle. Disclosure #I of this series (titled "A Strong Diaphragm/Safe Needle Unit and Components For Transfer of Fluids") describes how this may be accomplished by customizing needles and lessening the degree of diaphragm prechannelling/preweakening at the time of manufacture or irreversibly applying increased compressive pressure. Disclosure #III of the series (titled "Reversibly Compressed Prechannelled/Preweakened Diaphragms For Use With Blunt Cannulae and Safe Needles") describes the reversible augmentation of compressive pressure at the time of manufacture which is relieved at the time of first clinical use (i.e., prior to the insertion of a blunt cannula of the prior art or with one of the safe needles which characterize our series of disclosures).

The convertors described in the present disclosure will be customized (with respect to features such as sharpness, length, diameter, and configuration) to provide needle/ diaphragm/convertor combinations which seek to achieve our goals with respect to diaphragm function and needle safety. The sharpest component of such a system is the convertor. Handling and discarding of this device is much safer than handling a standard hypodermic needle or the aforementioned spike adaptor (that has been recommended for use with needleless systems) because, in contrast to the other devices, the convertor is not typically exposed to contaminants which pose a risk to a healthcare worker (since the convertor is used with previously unused diaphragms). As illustrated by several of the embodiments, another advantage of the use of a convertor is that it allows for the maintenance of a wholly intact (unindented, nonpierced) top surface of the diaphragm. This maintains sterility of the underlying contents and facilitates antiseptic swabbing. Even after penetration by the convertor, the diaphragm remains more resealable than after being torn by a blunt cannula. When indicated, the convertor can be constructed so as to only partially penetrate the diaphragm (as may be indicated if one wishes to maintain a vacuum in an underlying tube or vial). Although unnecessary in most embodiments, it can be lubricated so as to facilitate penetration and/or resealing; however, the indication should be far less than for traditional needlelesss systems. In addition, the convertor can be constructed so as to leave an indication (e.g., a mark or indentation) that the diaphragm has been converted.

In preliminary testing, we have shown that use of a 19-gauge pointed converting device can convert a conventional diaphragm which had been designed for use with a standard hypodermic needle to a diaphragm through which a partially blunted, recessed-orifice, 22 gauge or 24 gauge needle (but not a blunt cannula) can be inserted. Blunt cannula penetration requires conversion with a specially configured (e.g., larger diameter or slitting rather puncturing) convertor and/or by the concomitant use of a partially punctured or preweakened diaphragm. It should be noted that, while a standard hypodermic needle theoretically could be used to pierce a diaphragm, it has not been designed for, nor recommended for, this purpose. Specifically, the closed tip convertor configurations are preferable in that they minimize tearing and coring and avoid any chance of retaining an inoculum. Moreover, they can be matched with a given diaphragm and/or needle (or cannula) so as to optimize the features of the needle/diaphragm combination.

By utilizing the inventive needles (which are described below and detailed in Disclosure #I) as opposed to blunt cannulae, the present invention allows for maintenance of a smaller diaphragm opening and/or a lesser degree of diaphragm weakening. This substantially prevents unwanted communication between contents and environs, allows the inventive diaphragm to remain suitable for repeated use with regular as well as inventive needles (thereby obviating the need for multiple sets of supplies and bulky adaptors), and allows the inventive diaphragms to be constructed in a wide range of sizes (which may be adapted to meet medical needs without requiring a spike adaptor or standard sharp needle or the need for multiple stopper layers and leak-preventing valves).

The intrinsically safer inventive needles—which are far more versatile than the blunt cannulae of needleless systems—are achieved by customizing needles with one or both of the following:

(a) a partially blunted "safe" tip which is sharp enough to puncture the inventive diaphragm but not sharp enough to penetrate the skin under normal clinical conditions, including incidental contact or contact during recapping;

(b) a closed tip and one or more recessed orifices to minimize exposure to a sizable inoculum should superficial skin penetration occur. The increased safety afforded by the closed tip allows for the safe use of needles which are significantly more pointed than the blunt cannula of needleless systems and thus usable with a wider range of diaphragms and in a wider range of lengths and diameters. In addition, the solid tip lacks the "cutting" quality of an open-tip design and thereby should allow for more effective leak-free engagement and resealing. Moreover, to date, all reported transmissions of AIDS via puncture wounds to healthcare workers have resulted from puncture with a hollow bore device such as a traditional hypodermic needle or a broken glass tube. These present a sizeable inoculum which may be avoided with the solid-tip needles described herein.

Solid-tip needles are commercially available from many manufacturers for a variety of uses, including: spinal myelography, injection of intraspinal anesthetics, soft tissue biopsy, and perineural injections, as summarized by the present inventors in U.S. Pat. No. 5,478,328 in 1995 in which we taught that the use of a recessed-orifice needle permits the use of catheters which can be rotated to selectively overlie the needle orifice(s). No other inventor or manufacturer has even proposed the use of the recessed-orifice configuration for the purpose of healthcare worker safety, including the inventors of the following patents (U.S. unless noted otherwise): Leiter 145,217; Mitchell and Gillespie 561,059; Gillman 1,526,595; Weyl 446,818 (German); Peterson 2,097,039; Hanson 2,634,726; Gewecke 2,862,495; Morgan 1,196,601 (French); Schofield 3,181,336; Guttman 3,509,880; Jamshidi 3,882,849; Choksi 4,058,121; Sampson 4,190,048; Galindo 4,411,657; Guttman 4,413,993; Johnson 4,710,180; Sprotte 3,020,926 (German); Foran 4,767,407. These references disclose one or more of the following objectives: (1) to avoid coring of a rubber diaphragm by an open-bevel needle; (2) to minimize trauma to a patient's tissues; (3) to decrease the likelihood of harmful intraneural injections during infiltration with local anesthetic; (4) to provide an additional orifice to allow venting; (5) to provide a special needle hub; and (6) to improve the success of intravenous cannulation. For example, Hanson (2,634,726) discloses a needle with a chisel-like point and a single recessed orifice which opens obliquely on the side of the shaft ipsilateral of the convex side of the needle point and is said to minimize the likelihood of clogging the needle and injecting a cork or rubber core into a patient. In 1983, Galindo (4,411,657) disclosed a needle with a solid tapered tip and recessed orifice introduced to decrease nerve trauma during injection of local anesthetic. In that same year, Guttman (4,413,993) claimed his recessed-orifice needle for minimizing infiltration from the cannulated vessel during intravenous infusion of fluid (even if the tip of the needle extended beyond the back wall of the vessel). In 1985, Alchas (4,537,593) introduced a recessed-orifice needle with an overlying sleeve to allow venting during transfer of liquid to or from a container. In 1987, Johnson (4,710,180) described a blunt-tipped cannula with multiple recessed orifices for injecting fat cells into the skin after an incision was made to allow cannula insertion. Sprotte (Germany No. 3,020,926) introduced a modified recessed-orifice needle for spinal anesthesia with improved flow characteristics and a lesser incidence of dural tear and postspinal headache.

Thus, the present disclosure teaches new needle/diaphragm combinations with needle designs which not only are different from standard hypodermic needles but also differ significantly from those for the Baxter and Abbott needleless systems described above. Moreover, in contrast to the one-step process which is carried out in needleless systems solely at the time of manufacture (described by the prior art), the present disclosure introduces: 1) conversion of an intact diaphragm at the time of initial use; and/or 2) a two-step process which entails partial prechannelling (e.g., partial prepiercing or partial preslitting) and/or partial weakening at the time of manufacture followed by penetration by a convertor just prior to clinical use. Thus, the diaphragm may be minimally compromised at the time of manufacture, yet readily penetrable by an inventive needle or cannula at the time of clinical use.

This disclosure also teaches a combined testing procedure which addresses both testing of diaphragm integrity and penetrability as well as relative needle safety using a combined index (described below).

A further feature of the invention is to provide a needle and diaphragm combination which is amenable to user friendly, efficient external modifications to decrease the likelihood of healthcare worker exposure to contaminated fluids even in the absence of a needle stick—e.g., retractable caps and sheaths disclosed in Disclosure #I ("Strong Diaphragm/Safe Needle Units and Components for Transfer of Fluids") and in U.S. Pat. No. 5,478,328, incorporated by reference.

BRIEF DESCRIPTION OF THE DRAWINGS

In FIG. 8c, an optional depression identifies the site for insertion of a convertor and/or needle and facilitates such insertion. FIG. 8d shows an optional depression surrounded by a circumferential ridge.

FIG. 11a shows that the rim around the diaphragm and its housing may be configured to provide increased axial compressive pressure and thereby help to maintain diaphragm integrity. FIG. 11b shows that the entire diaphragm or simply the region which included the prechannelled or preweakened site may be made with increased thickness to maintain diaphragm integrity. FIGS. 11c–11d illustrate the presence of an additional membrane which may itself have a slit or simply provide additional thickness. FIG. 11e is another embodiment which illustrates a way to minimize the effect of prechannelling (or preweakening) on diaphragm integrity; increased compressive force is provided by a tight-fitting band. The band may remain permanently in place (Disclosure #I and #II) or it may be removed to partially relieve the compressive forces prior to clinical use (Disclosure #III).

FIGS. 14a–14e show several embodiments of a convertor with: (a) a closed tip and a sharp pencil-like point; (b) a closed tip and sharp biased point and alternative gripping surface; (c) a sharp, open tip as might be found on a standard hypodermic needle; (d) a flange or flanges which make a slit or slits in the diaphragm; and (e) a closed tip and a sharp biased cutting edge which may be retractable into a grippable handle.

FIG. 24b shows a cap with the added protection of a shield which reduces the likelihood of unwanted advancement of the convertor.

FIG. 25a shows the central portion being supported by a removable band. In FIG. 25b, the band is attached via a serrated junction to the central portion of the cap which houses the convertor.

DETAILED DESCRIPTION OF EMBODIMENTS OF THE INVENTION

Figure 1:
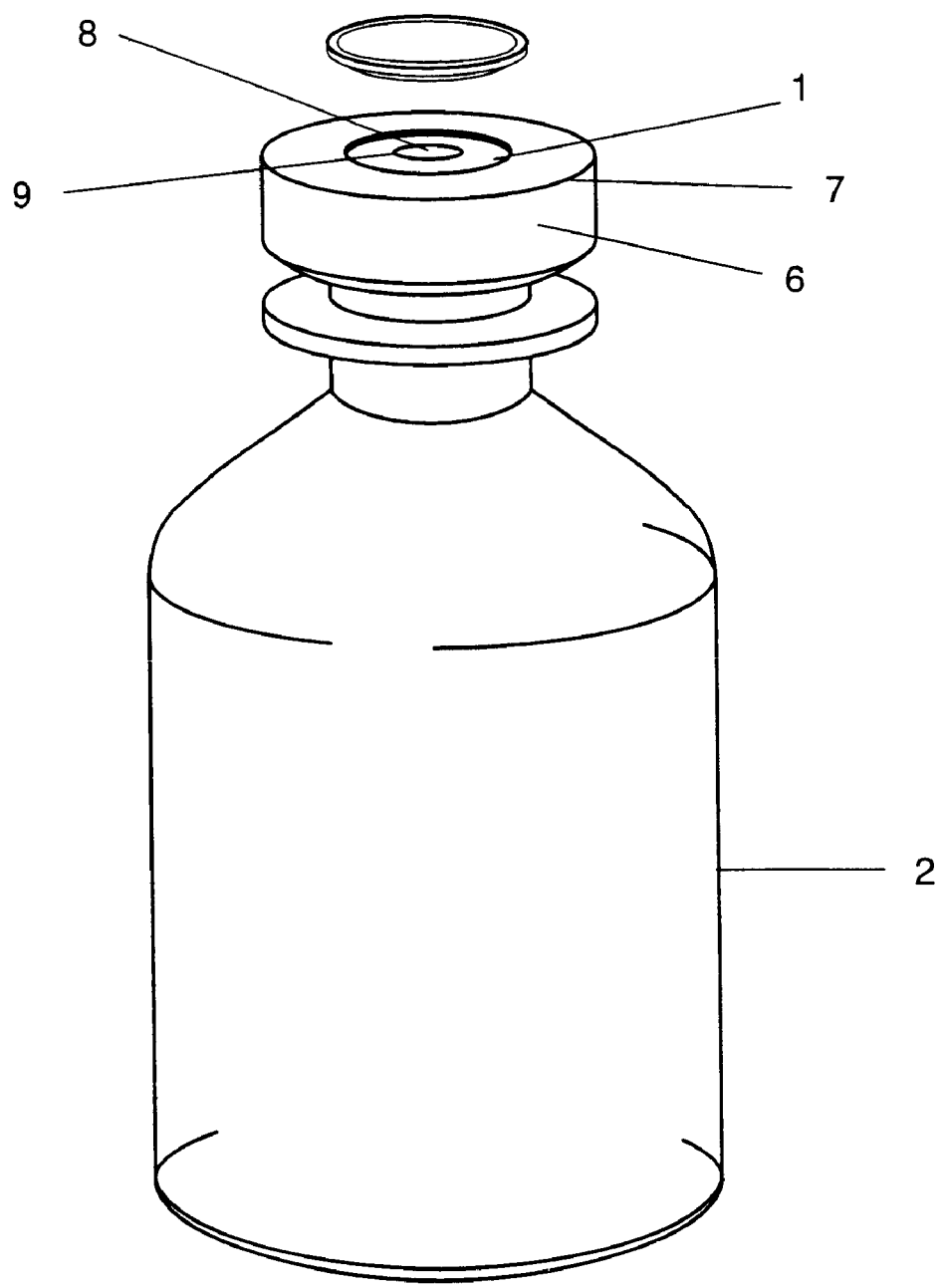
FIG. 1 shows a standard diaphragm on top of a typical medication vial.
Figure 2:
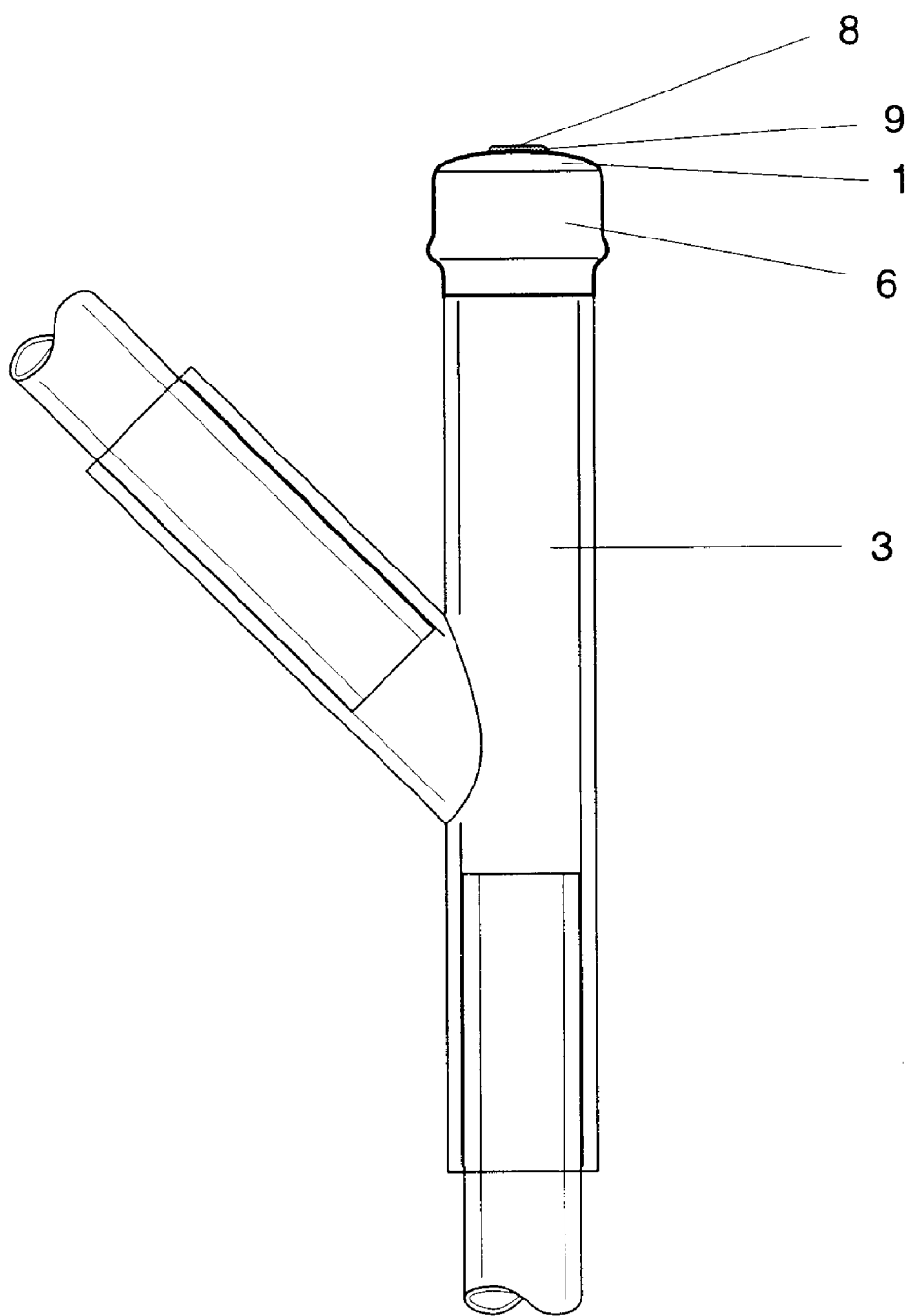
FIG. 2 shows a standard diaphragm on top of a standard injection port for intermittent infusion of medications and fluids via intravenous tubing which is connected to an indwelling intravenous catheter.
Figure 3:
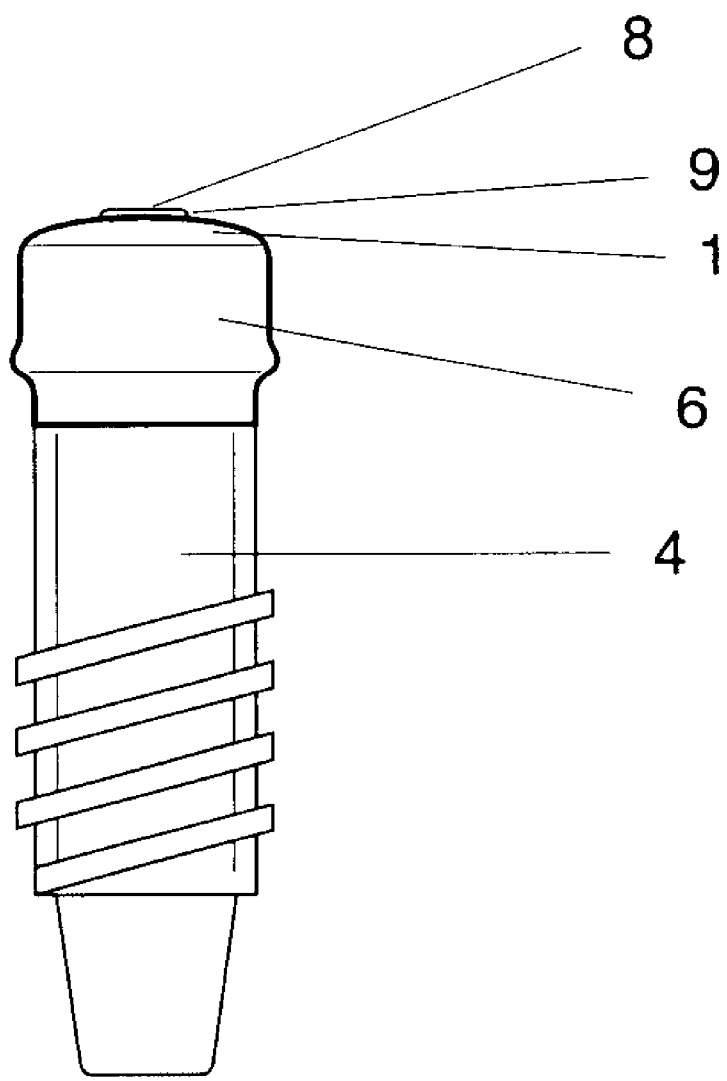
FIG. 3 shows a standard diaphragm on top of an adaptor for penetrable plugging of the nonpatient end of an indwelling catheter (e.g., a standard heparin lock for intermittent intravenous infusion of drugs).
Figure 4:
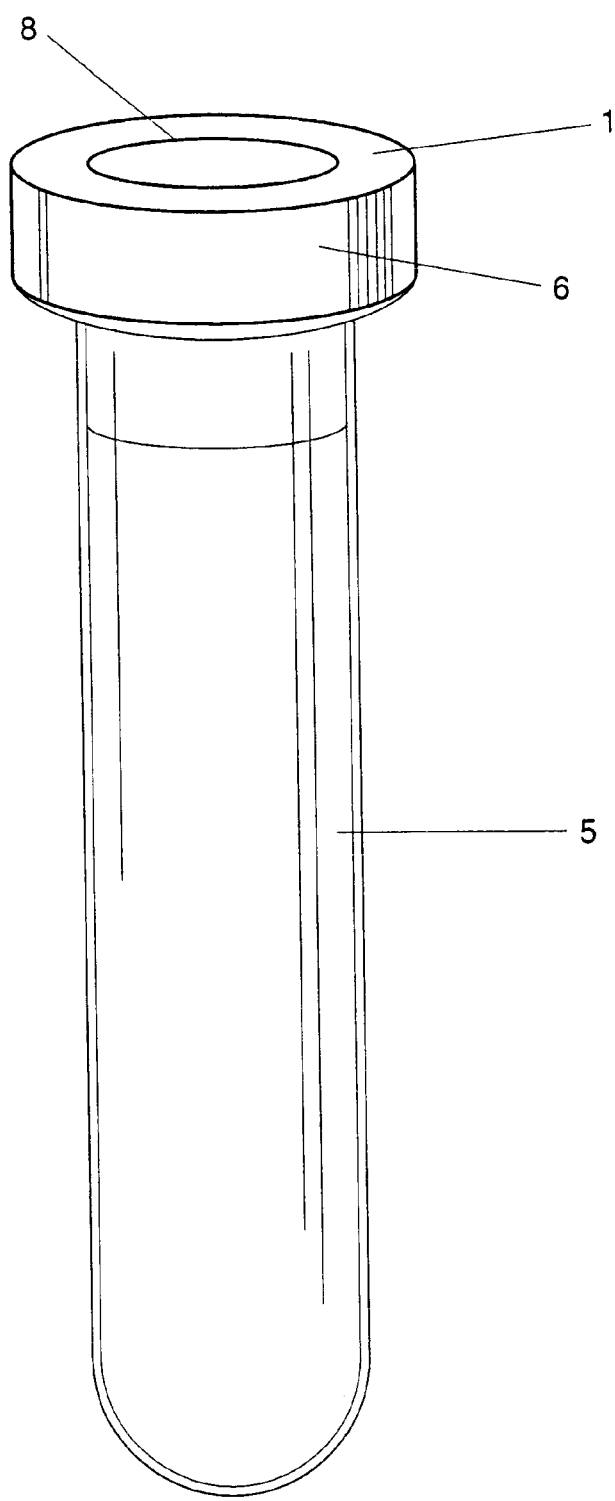
FIG. 4 shows a standard diaphragm on top of a standard vacuum tube for blood collection from a needle attached to a filled syringe or by attachment to a vacuutainer blood collection system.

The following description of embodiments of the invention refers to the accompanying drawings. It will detail features of the diaphragms, convertors, and safety needles. Other objects, features, and advantages of the present invention will become apparent from this description. It should be noted that we will not attempt to reteach aspects that already have been described in the prior art, such as the construction of a standard diaphragm, standard needle, or blunt cannula. It also should be noted that, although some of the individual components described in the present disclosure may in and of themselves not be unique, their use in combination has not heretofore been known. Thus, when we describe an individual component, a major distinguishing feature of the component may entail its use in combination with a given convertor and/or needle or another component (and the testing of such combinations). Further, modifications, equivalents and adaptations of specific features and of the combinations of features from the specific embodiments described below are intended to be within the spirit and scope of this disclosure.

Diaphragms

The diaphragms of the present invention are designed to:

a) maintain their integrity prior to clinical use;

b) be readily penetrable to inventive needles at the time of clinical use;

c) demonstrate effective leak-free engagement and sealability during and after such use. These goals are achieved with a series of inventive diaphragms which remain intact or undergo only slight compromise (preslitting or preweakening) prior to clinical use.

The diaphragm may be composed of a number of different materials. Soft, impermeable, easily penetrable, resilient materials are preferred so that the diaphragm: 1) provides effective, leak-free closure; 2) has the penetrability, resilience, and memory to allow efficient insertion of the desired needles or cannulae after the converting procedure; 3) engages the needle effectively; and 4) has sufficient memory and resilience to reseal effectively. As noted by Sims in U.S. Pat. No. 4,846,809, diaphragms should be formed with sufficient memory so that an opening formed by a penetrating needle point will tend to close after the needle tip has been retracted beyond the membrane. Polyisoprene rubber is a preferred form of resealable rubber, although resealable latex, silicone or butyl rubber may be used. Brimhall (U.S. Pat. No. 5,242,393) has described the use of an elastically deformable thermoset elastomer, preferably Dow Corning Medical Grade Injection Moldable silicone rubber. Donnelly 4,513,651 taught a stopper that is a composite inner elastomer core and an annular surround plastic cap. Grippi 4,697,717 describes a stopper that is a composite of plastic and rubber.

In each of the embodiments, the diaphragm is housed in a retaining member. This typically is a cylindrical housing, but it may take on other forms so long as it applies axially directed forces to the sealing member. The cylindrical housing may be tapered at the top in order to promote sealing of this region and to provide a curved exterior peripheral surface under suitable pressure. Kleiner 2,607,347 (in 1952)

taught that "By having the plug portion of slightly larger diameter than the bore which receives it, that portion is placed under compression as the stopper is positioned." This has served as a basic feature of the prior art.

Figure 5A:
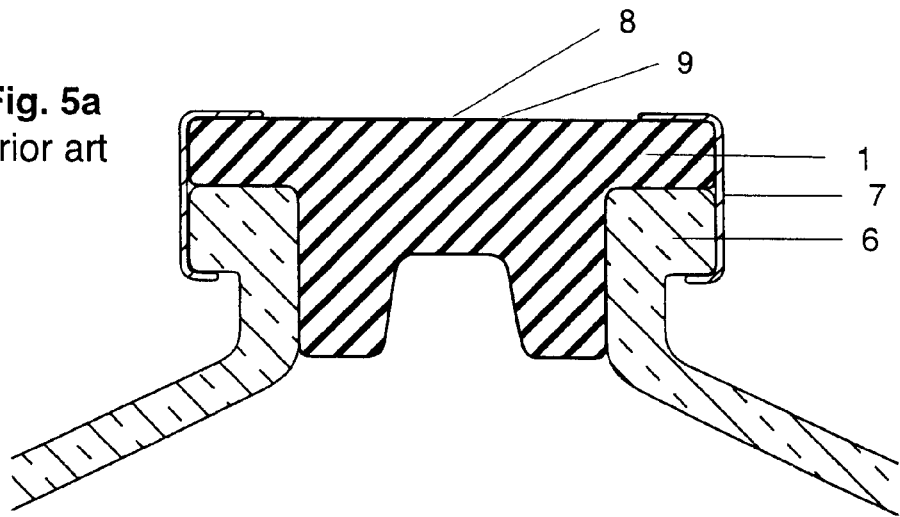
FIGS. 5a–5c are cross-sectional views of an intact (i.e., non-slit, non-weakened) compressible diaphragm which is maintained under compressive pressure in one of many potential housings which are usable in FIGS. 1–4 above.
Figure 5B:
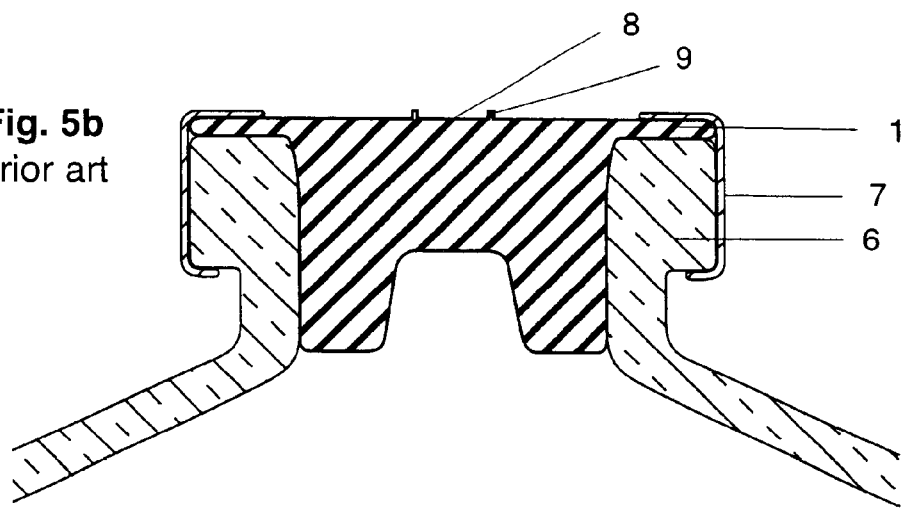
Figure 5C:
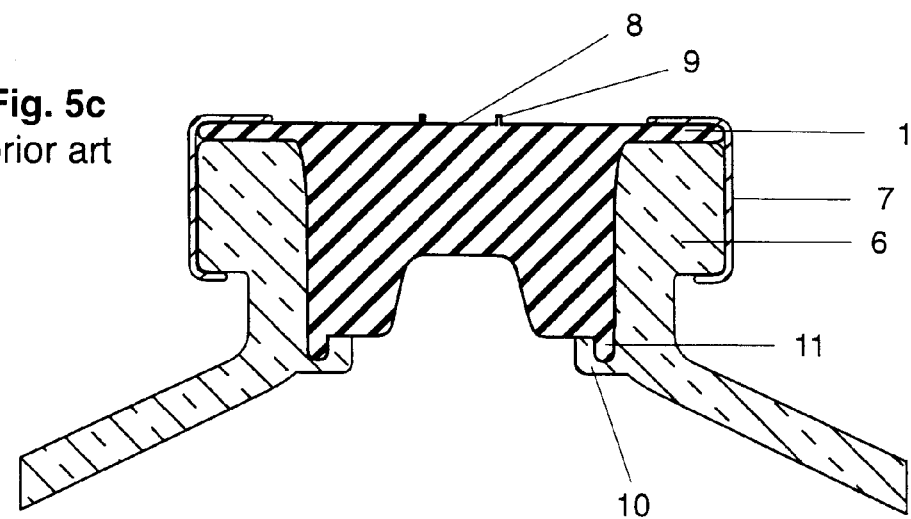

FIGS. 1–5 show standard diaphragms 1 as taught by prior art on top of a typical medication bottle 2, an i.v. tubing injection port 3, a heparin lock for drug infusion (4), and a vacuum tube for blood collection 5. The receptacle 6 in which the diaphragm is retained 6 provides for compressive engagement and retention. As illustrated in FIG. 5, the diaphragm may extend to varying degrees (if at all) above the receptacle 6. Retention of the diaphragm may be augmented by a rim 7 around the circumferential surface of the diaphragm. Diaphragms typically have a "soft spot" 8 which is surrounded by a raised border 9. This is the preferred site for penetration with a standard hypodermic needle or with a convertor as described in the present invention. The configuration of the portion of the housing below the receptacle will depend on the nature of the underlying structure (e.g., bottle vs. i.v. tubing injection port). This portion of the housing can also be constructed so as to accommodate the displaced diaphragm when it is deformed by penetration of a needle or cannula. FIG. 5c shows a lip 10 in the housing which creates a channel 11 for this accommodation. (For purposes of simplicity, such a feature is not included in most illustrations of the prior art or of the present invention.)

Figure 6A:
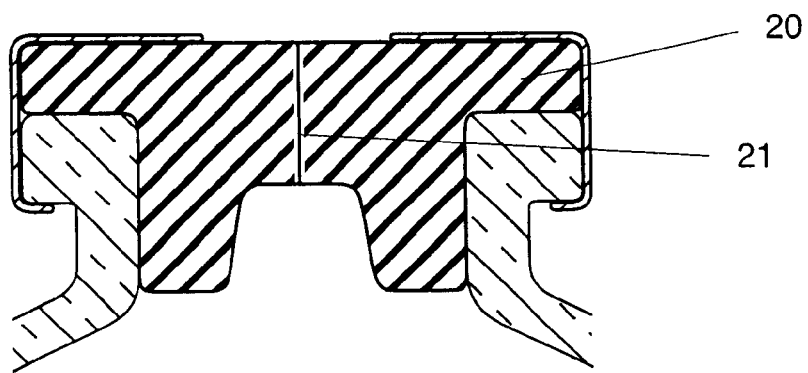
FIGS. 6a and 6b are cross-sectional views of different forms of preslit diaphragms that have been taught by the prior art, wherein the slit (which is imparted at the time of manufacture) extends all the way through or almost all of the way through the diaphragm.
Figure 6B:
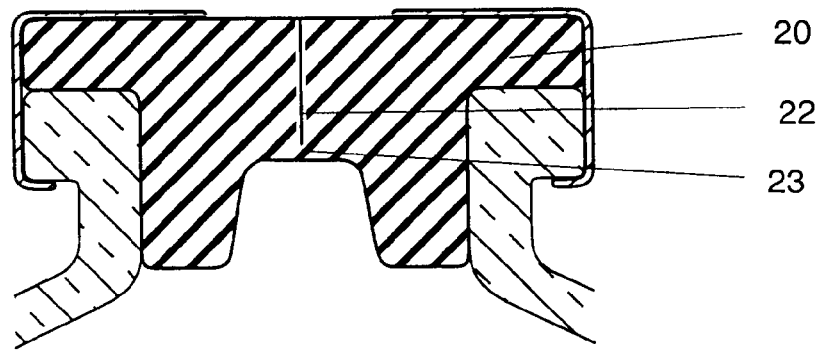
Figure 7A:
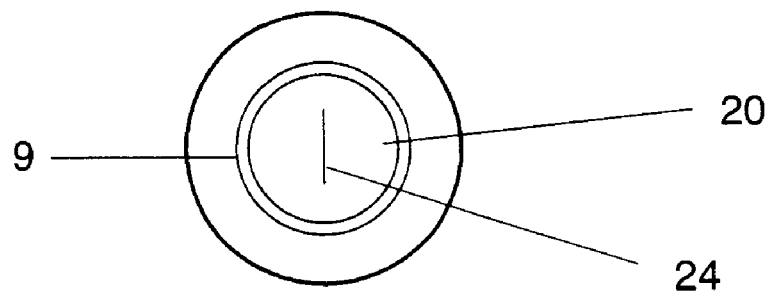
FIGS. 7a and 7b are top views of preslit diaphragms which illustrate slits as they appear in embodiments of the prior art.
Figure 7B:
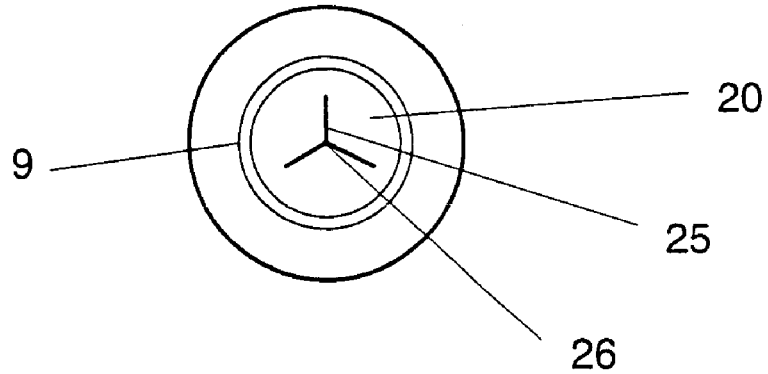

The prior art has shown that, for needleless systems, a diaphragm may be altered at the time of manufacture to allow penetration by a blunt cannula. FIGS. 6 and 7 show prior art diaphragms 20 which have been manufactured for penetration by a blunt cannula such that they contain a slit which extends through the entire thickness of the diaphragm 21 or a slit which extends substantially therethrough 22, so as to leave a small tearable region 23. As shown on the top view (FIG. 7), the penetrable area may consist of a single slit 24 or an array of slits 25 such as the three-armed cut, the arms of which are at 120° to each other 26. The prior art taught the creation of a slit that was long enough, wide enough, and deep enough to allow insertion of a blunt cannula and to minimize the need for excessive force and increased risk of tearing. However, the size of the slits was limited by their ability to ensure effective leakfree engagement and subsequent resealing. Jepson et al. WO 90/11103 taught that the length of the slit(s) should be <½ the circumference of the cannula being inserted therethrough. Such a requirement also limited the size of the cannula; i.e., a wide cannula would require a large slit and thus the integrity of the diaphragm would be compromised even before cannula insertion.

FIGS. 8–10 show embodiments of the present invention wherein the inventive diaphragm 30 has undergone a lesser degree of prechannelling than was required for the blunt cannula penetration taught by the prior art. FIG. 8a is a cross-sectional view of an inventive diaphragm 30 which shows a slit 31 which is biased in the closed position by forces as may be generated by the receptacle. Said slit extends from the top surface 32 through significantly less of the thickness of the diaphragm than the slits of the prior art. FIGS. 8b–8d show how a partial preslit 31 may arise from the bottom 33 of the diaphragm 30 (and thus leave an intact, easily cleanable top surface) or from an indented region 34 at the top of the diaphragm 30. According to the present series of disclosures, such partial preslits 31 could be deepened by use of a convertor (Disclosure #II), widened by release of compressive forces (Disclosure #III) or could use a relatively pointed safety needle (as described in Disclosure #I). The channels and housing can otherwise be consistent with the prior art. Consistent with the prior art, the height of the septum can be, for example, on the order of 0.125 inches (0.318 cm).

Figure 8A:
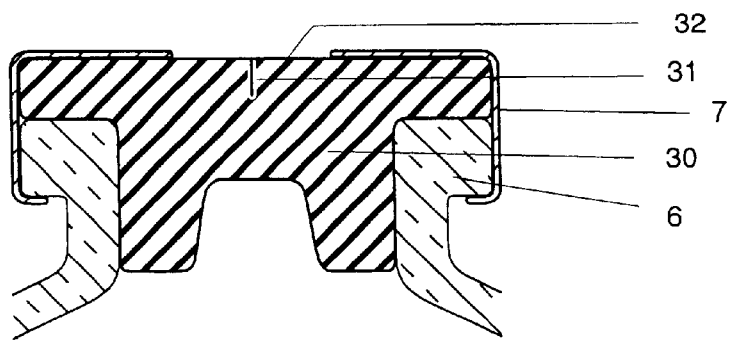
FIGS. 8a–8d are cross-sectional views of embodiments of the present invention wherein the diaphragm is preslit to a lesser degree than was required for subsequent blunt cannula penetration as taught by the prior art.
Figure 8B:
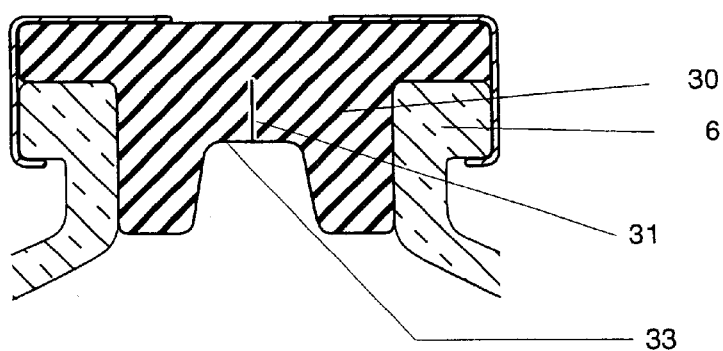
Figure 8C:
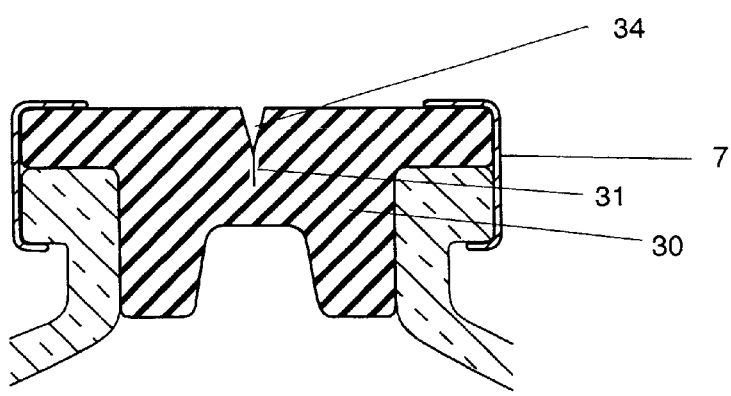
Figure 8D:
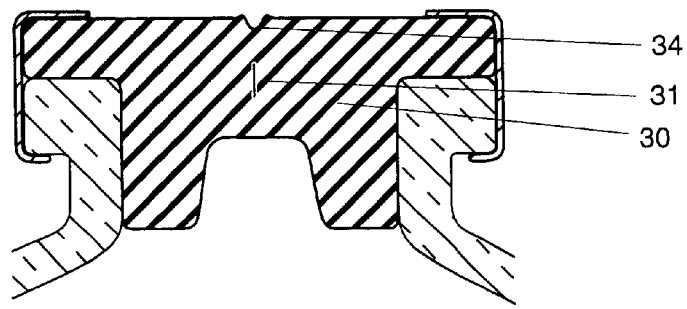
Figure 9A:
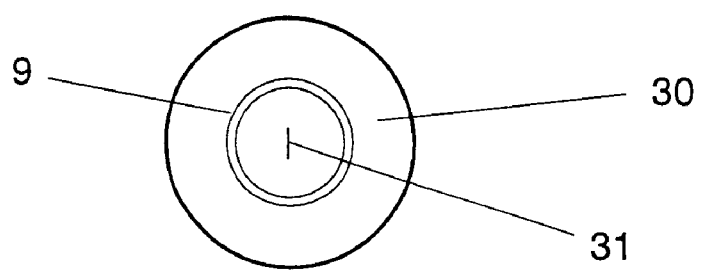
FIGS. 9a–9d are top views as they appear in embodiments of the present invention in which the preslits are incomplete and/or smaller (e.g., shorter, thinner, and/or less deep) than those required for the blunt cannula insertion of the prior art. Thus the diaphragm is weakened only slightly (in contrast to the more pronounced preslitting of prior art blunt cannula diaphragms). Likewise, in each of the configurations, the slit may lie totally beneath the diaphragm surface. According to the present invention, the preslits could be extended by use of a convertor (or, as described in Disclosure #I of this three-part series, would require the use of a relatively pointed safety needle since they would not be penetrable by a blunt cannula).
Figure 9B:
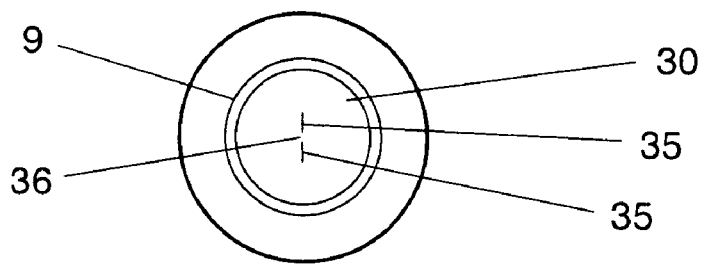
Figure 9C:
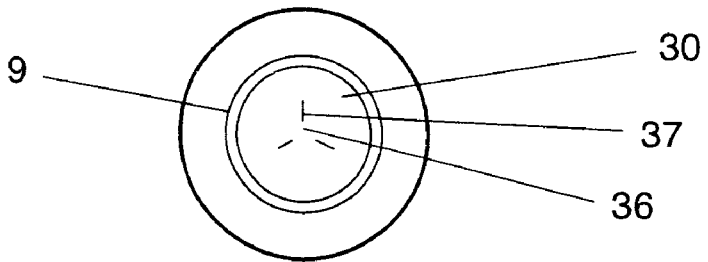
Figure 9D:
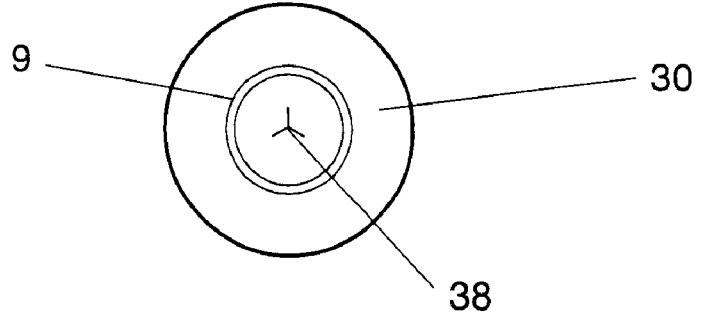

FIGS. 9a–9d are top views which illustrate embodiments of the present invention in which the channel(s) is (are) shorter than that of the prior art and can be lengthened and/or widened by insertion of a convertor (or needle). Consistent with the prior art, in each of the illustrated embodiments, the site of penetration is surrounded by a raised rim or flat visual identifier 9 such as a colored circle. FIG. 9a shows an embodiment of the inventive diaphragm 30 with a small slit 31. FIG. 9b shows a diaphragm 30 in which a divided slit 35 has a gap 36. FIG. 9c shows a gap 36 which needs to be pierced in order to extend and unite the arms of an array of partial slits 37. FIG. 9d illustrates an array of short slits 38 which may be enlarged by a convertor or needle. For purposes of clarity, each of the embodiments shows the slit(s) extending to the top surface; however, the slit(s) may remain below the surface (as shown in FIGS. 8b and 8d) and thus leave the upper surface totally intact.

Figure 10A:
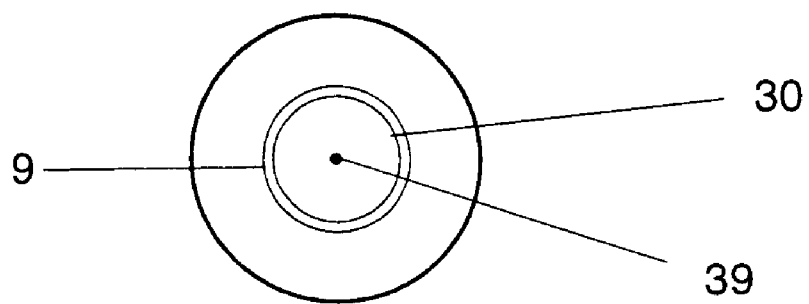
FIGS. 10a–10b are top views as they appear in embodiments of the present invention in which the diaphragm has been constructed such that the partial prechannelling entails creation of a partial hole rather than a preslit at the time of manufacture. Such a hole may lie totally beneath the surface (as suggested by the shading in FIG. 10b).
Figure 10B:
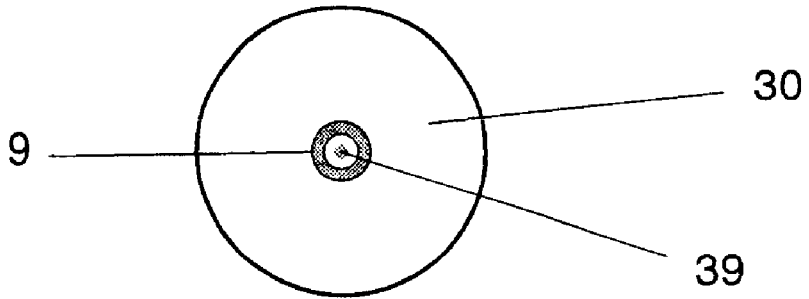

FIGS. 10a and 10b illustrate a hole 39, as opposed to a slit, which may be sufficient when an inventive needle (or convertor) is inserted through a diaphragm 30. Said hole 39 may extend from the surface through the entire thickness of the diaphragm 30 or it may extend only partway through and even lie below the surface. In the illustrated embodiment, the rim 9 encircles the recommended site of penetration. The diameter of said rim 9 can be reduced (as in FIG. 10b) to improve the accuracy of needle insertion. A marking or depression similarly may be used to identify the optimal site of insertion.

Figure 11A:
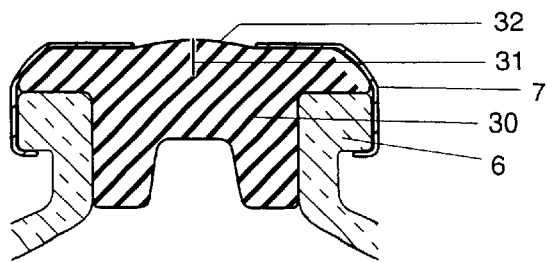
FIGS. 11a–11e show ways of maintaining diaphragm integrity despite the presence of a prechannelled region.
Figure 11B:
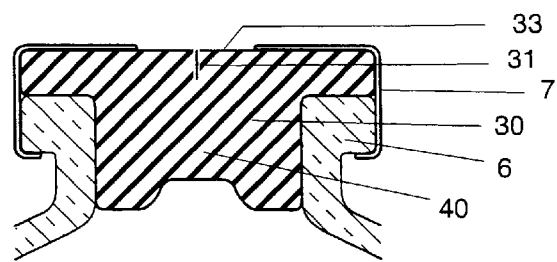
Figure 11C:
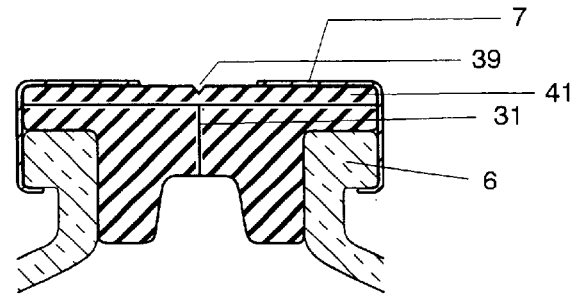
Figure 11D:
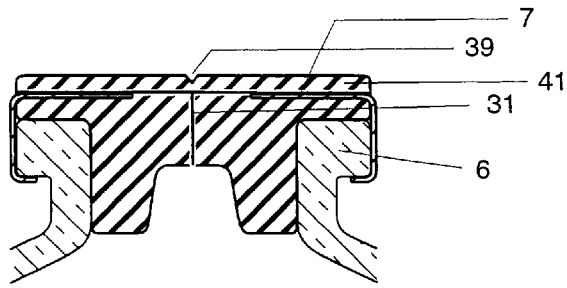
Figure 11E:
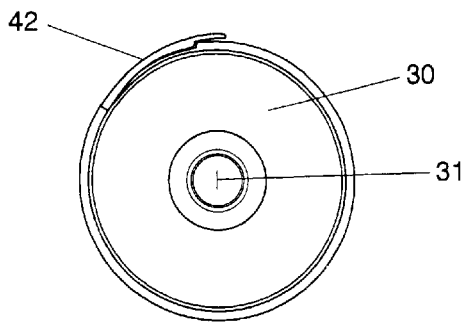

FIGS. 11a–11e illustrate arrangements for maintaining the integrity of a prechannelled diaphragm while still allowing penetration by a tapered needle or convertor. FIG. 11a shows that this may be accomplished by increasing axially directed compressive forces as may be achieved by inwardly curving the retaining (compressive) rim 7; this typically causes the top surface 32 to bulge outward. Other means of increasing diaphragm integrity include: increasing the thickness of the region 40 of the diaphragm 30 that is below the prechannelled site 31 (FIG. 11b); providing an overlying membrane 41 which may lie above (FIG. 11c) or below (FIG. 11d) the rim 7; compressing the diaphragm 30 and its housing with a tight band 42 (FIG. 11e).

Figure 12:
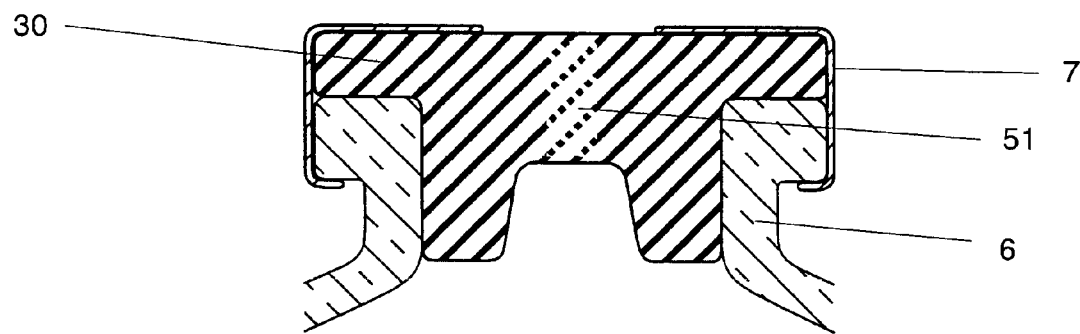
FIG. 12 is a cross-section of a diaphragm which has undergone ultrasonic weakening as described in the prior art.
Figure 13A:
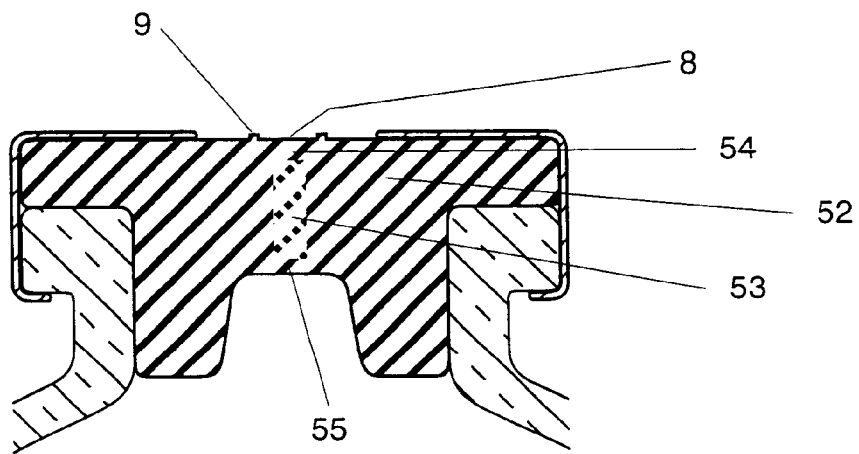
FIGS. 13a and 13b show embodiments of the present invention wherein the diaphragm has undergone ultrasonic weakening to a lesser degree than was required for blunt cannula penetration as taught by the prior art.
Figure 13B:
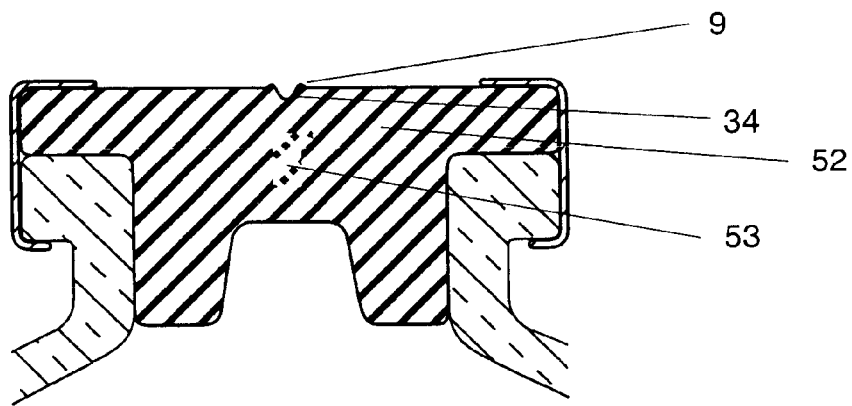

As noted in the prior art and illustrated in FIG. 12, prior art diaphragms designed for use with blunt cannulae may have a weakened area 51. One way in which this may be accomplished is by ultrasonic heating. FIGS. 13a and 13b show embodiments of the present invention wherein the inventive diaphragm 52 has a region 53 which has undergone ultrasonic weakening to a lesser degree than was required for blunt cannula penetration as taught by the prior art. The inventive series would allow this to be accomplished to a lesser degree by such methods as decreasing the joules generated per second or decreasing the duration for which the ultrasonic energy is applied until the diaphragm is just weak enough to allow use with the inventive needles or convertors. The integrity of the outer upper 54 and lower 55 portions may be better maintained by accelerating the removal of heat from these areas by increasing heat removal from the anvil and the horn as may be accomplished by increasing heat conductivity of said anvil and horn or cooling them with an external heat sink such as a water bath. The weakened area may be beneath a standard target site 8 or a depressed site 34 on the surface, each of which may be surrounded by a rim 9. An indentation not only identifies the site for insertion but it also forms a partially prechannelled region.

Convertors

The convertors of the present invention are designed to change a diaphragm such that:

a) a standard diaphragm becomes penetrable by one or more embodiments of the series of partially blunted inventive needles (without the need to compromise the diaphragm in any way prior to the first clinical use);

b) a partially prechannelled inventive diaphragm with a partial (incomplete) preslit or hole becomes penetrable by a wider range of partially blunted needles and perhaps even by a blunt cannula; or c) a partially preweakened inventive diaphragm becomes penetrable by a wider range of partially blunted needles and perhaps even a blunt cannula.

In each of the embodiments, the convertor contains a sharp or partially sharp end which is designed for diaphragm penetration such that subsequent penetration by an inventive needle or blunt cannula is facilitated. In contrast to standard hypodermic needles and to the adaptor spikes of needleless systems, the inventive convertor typically does not contact (or, in the worst case, does not remain in contact with) a potential inoculum which would pose a risk of infection to healthcare workers in any of its anticipated uses.

As shown in FIGS. 14a–14e, the relatively simple embodiments of a convertor can take on several different forms and thereby create different degrees of change in the diaphragm. Each of the convertors which is shown has a shaft 70, a gripping end 71 or handle 72 and a tip. The tip may be designed as: (a) a closed, sharp pencil-like point 73; (b) a closed tip and sharp biased point 74; (c) a sharp, open tip 75; or (d) a flange(s) 76. While closed-tip embodiments are preferred because they add an extra degree of safety and decrease the likelihood of diaphragm coring, an open-ended device is acceptable (since a convertor is not intended for use with infectious material). A convertor may be in the shape of a carpenter's nail; however, it is easier to handle if it contains a more grippable region (e.g., a hub 71 or handle 72). There are several ways in which the convertor can be configured to make a slit rather than a hole. A biased tip 74 can be advanced along its entire surface such that a slit is created. FIG. 14d shows a convertor with flanges 76; their insertion makes a slit or slits in the diaphragm. As shown in FIG. 14e, to increase user safety, the convertor can be designed so as to be retracted into its handle 77 as may be accomplished by depressing a button 78 which activates the retracting mechanism.

Figure 15A:
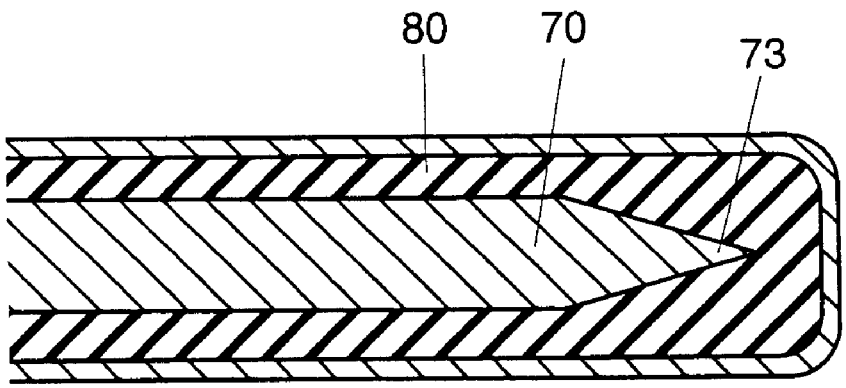
FIGS. 15a and 15b illustrate how a convertor may be covered by a retractable sheath.
Figure 15B:
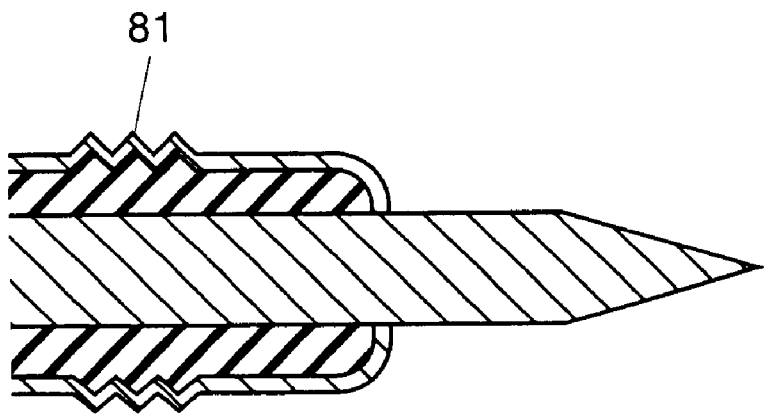

FIG. 15 illustrates how exposure to a convertor may be limited by covering its tip 73 with a retractable sheath 80. Said sheath will retract over the taper and shaft 70. It may be made of a compressive material such as latex or rubber, and it may contain a region 81 which is particularly compressible.

Figure 16A:
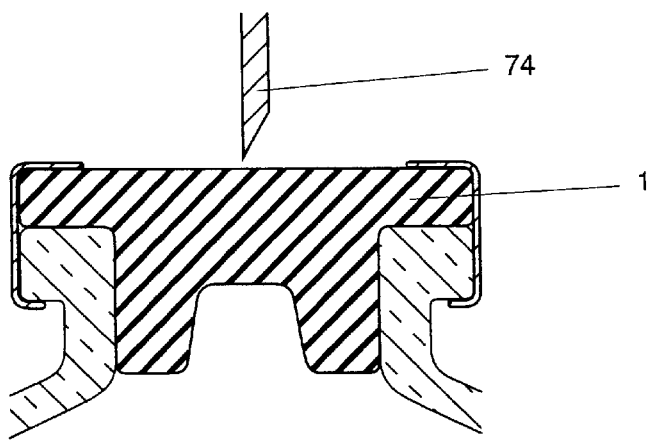
FIGS. 16a–16c show a convertor penetrating: (a) a standard diaphragm to enable use of an inventive "safe" needle; (b) a partially prechannelled diaphragm; (c) a partially preweakened diaphragm.
Figure 16B:
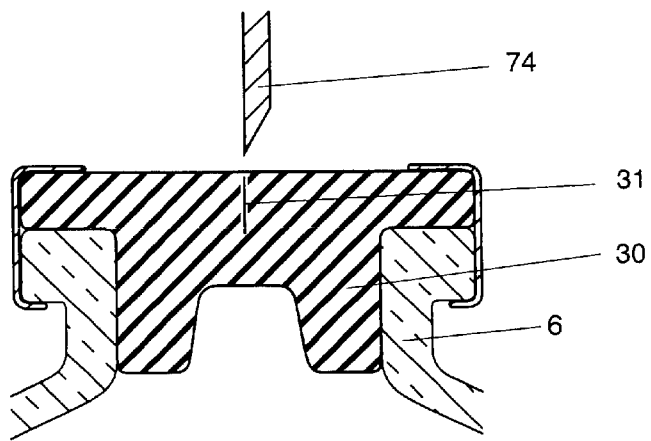
Figure 16C:
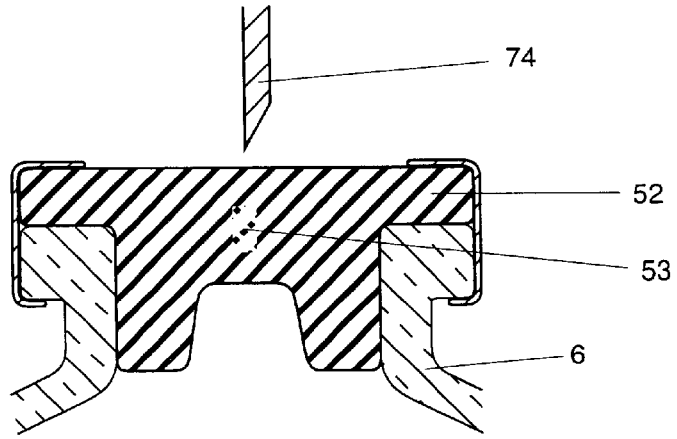

As shown FIGS. 16a–16c, the tip 74 of a convertor can be advanced through a diaphragm to (a) convert a standard diaphragm 1 into one with a channel; (b) a prechannelled diaphragm 30 into one whose channel 31 is of increased penetrability; and/or (c) a preweakened diaphragm 52 into one with a channel as well as a weakened region 53.

Figure 17:
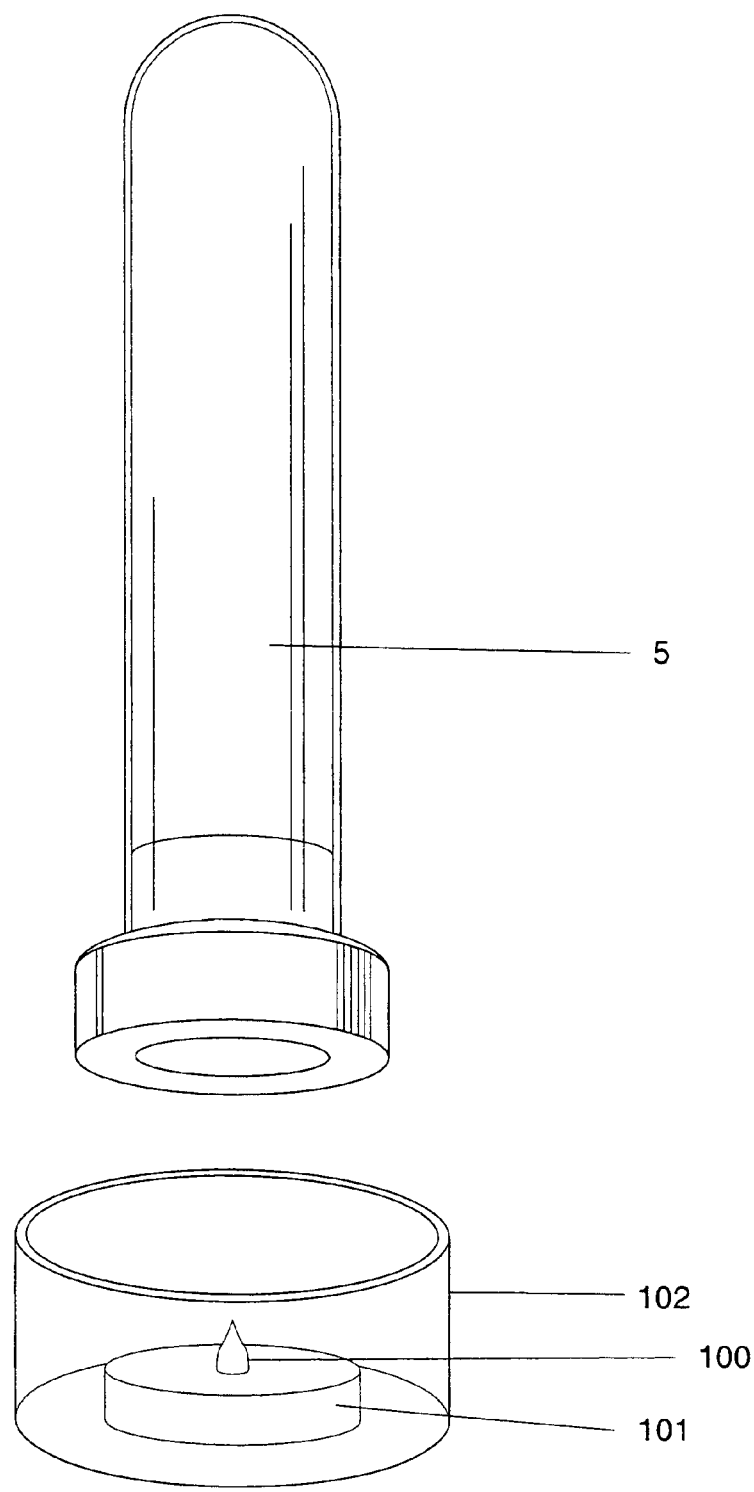
FIG. 17 shows a convertor which is attached to a foundation so as to provide a reusable device for rapid puncturing of multiple diaphragms. For use with a vacuum tube, such as the one illustrated, the length of the convertor may be such that it does not penetrate through the entire thickness of the diaphragm.

For purposes of efficacy and safety, a convertor 100 may be attached to a foundation 101 and/or incorporated within a housing 102. As illustrated in FIG. 17, this is well-suited for puncturing (converting) multiple blood sampling tubes 5. Said foundation 101 can be portable or mounted. The pictured device illustrates how the convertor 100 can be incorporated within a housing 102 and thus be shielded to minimize inadvertent sticks. Said housing 102 could be made of a variety of materials, including plastic comparable to that used to encase sampling tubes during actual blood withdrawal from a patient with the vacuutainer system. The width of the foundation 101, the height of the housing 102, as well as the length, width and pointedness of the convertor 100 can be adapted to the length, width and related qualities of the diaphragm(s) to be channeled (with a hole or slit) so as to optimize efficiency and safety. The outer surface of the item to be pierced and the inner surface of the shield can have matching alignments (e.g., grooves and tabs) to facilitate advancement.

Figure 18:
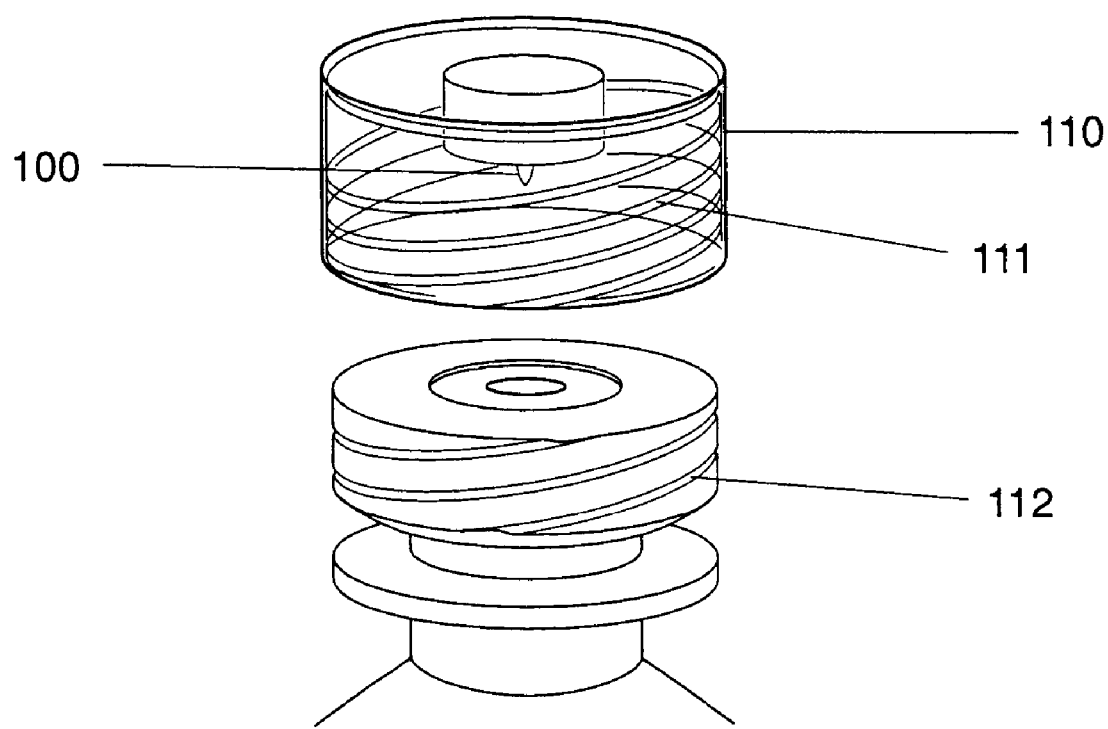
FIG. 18 shows an embodiment of the present invention wherein the convertor is incorporated into a cap which has been modified so that the top and the enclosed convertor can be advanced downward by a device such as threaded engagement.
Figure 19:
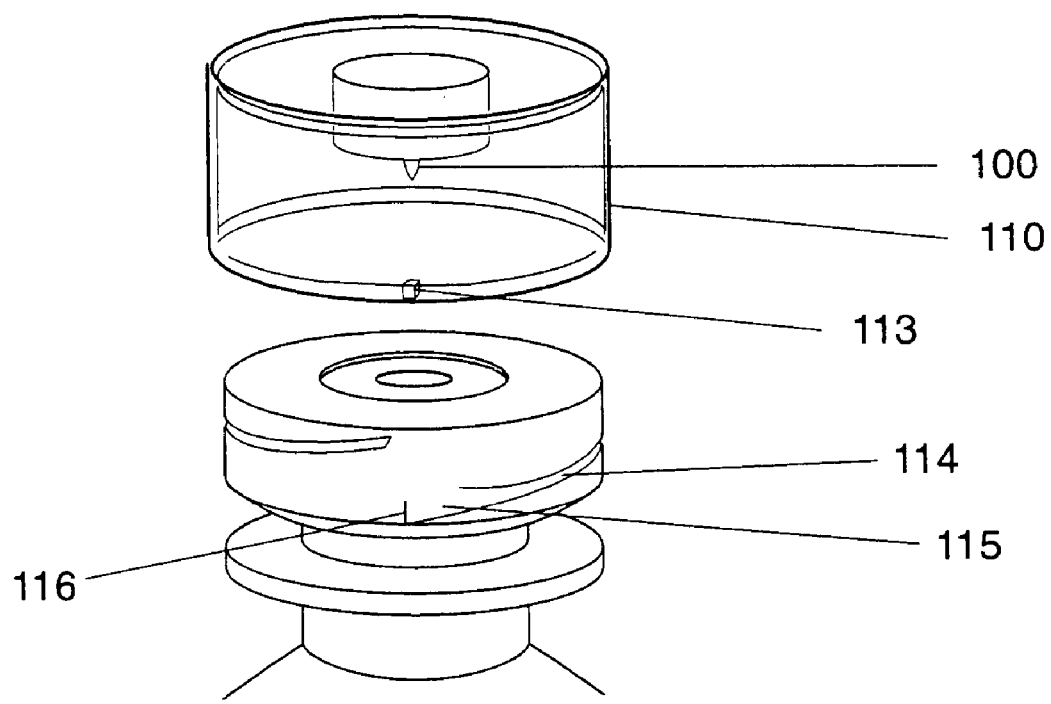
FIG. 19 shows an embodiment where a tab on the cap is advanced through a channel on the outside of the diaphragm and its housing such that depression of the cap and convertor leads to (and is required for) cap removal. Similarly, the tab can be on the outside of the diaphragm while the groove is on the inside of the cap.

FIGS. 18–27 show embodiments of the present invention wherein the convertor is incorporated into a cap atop a bottle or other form of housing that contains a penetrable diaphragm. The caps are designed to prevent accidental penetration prior to intended use. An example of a simple embodiment is shown in FIG. 18. The cap 110 containing the convertor 100 has threads (or grooves) 111 for engagement with matching grooves (or threads) 112 on the outside of the diaphragm housing. FIG. 19 shows that, to avoid the need for subsequent unscrewing in order to achieve cap removal, the cap 110 can contain a single tab 113 that is advanced downward through a groove 114 on the bottle top until it becomes aligned with an opening 115 at the end of the groove 114. This allows the tab 113 to be raised out of the groove 114 and for the cap 110 and its convertor to be removed. A backstop 116 may be included to identify the end of the groove 114. These mechanisms can similarly be accomplished by a variety of designs including: 1) a tab 113 on the outside of the diaphragm housing and a groove (or grooves) 114 on the inside of the cap 110 that houses the convertor 106; 2) an angled luer-lock mechanism (these are not shown).

Figure 20A:
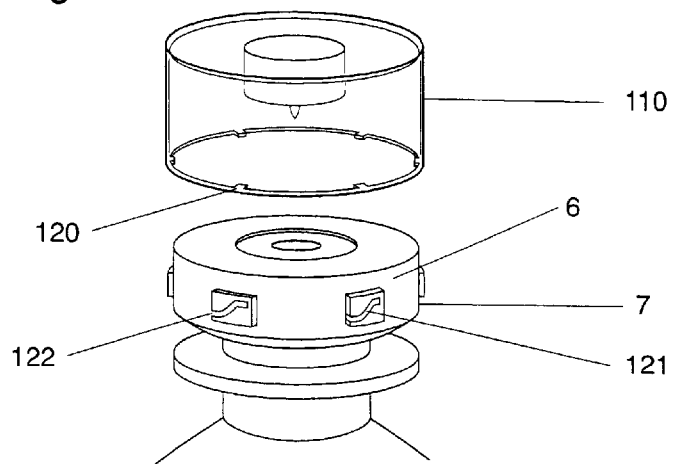
FIGS. 20a–20c show how tabs on one body (e.g., the cap) may be aligned with ridges on the other (e.g., the diaphragm housing) such that the inventive cap with convertor cannot be advanced and removed without navigating around the ridges.
Figure 20B:
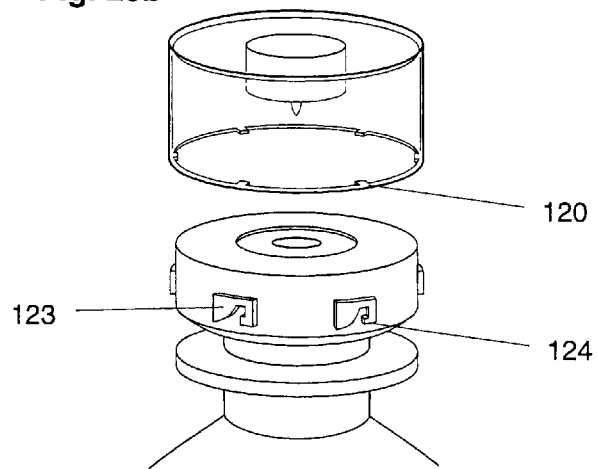
Figure 20C:
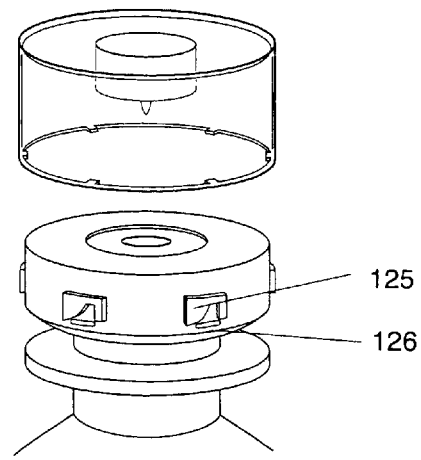

As shown in FIGS. 20a–20c, mechanisms to prevent unwanted convertor advancement may be obtained with designs comparable to those of "child-proof" pill bottles. Tabs 120 on the cap 110 are retained by one of many different potential configurations of grooves in rim 7 of the diaphragm housing 6. A deliberate turning maneuver is required in order to advance the cap 110. As for the top described in FIG. 19, the apparatus can be designed such that the advancing process is a necessary component of the steps for removing said cap 110. In FIG. 20a, the tabs 120 sit in a groove 121. As the cap 110 is turned clockwise, the tabs 120 are advanced through the groove 121 such that each tab 120 reaches the lower part of the groove 122 from which it may exit. This allows the cap to be removed. FIGS. 20b and 20c show grooves which restrict movement of the tabs and hence restrict removal or advancement of the cap and convertor unless there is the application of downward force and a deliberate turning motion. In FIG. 20b, each of the grooves 123 contains an angulated inferior rim 124. In FIG. 20c, the groove 125 has a backstop 126 which serves to restrict downward movement of the cap 110. The cap 110 also can be structured so that one needs to depress the side of the cap 110 in order to engage the tabs 120 in the grooves.

Figure 21A:
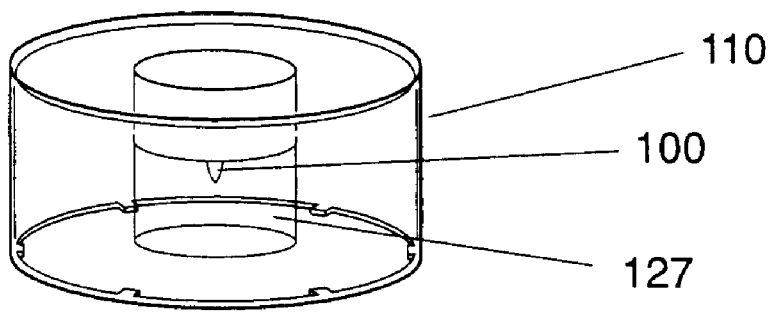
FIGS. 21a–21c show caps which contain a convertor that is within a compressible, collapsible, or displaceable supporting shield.
Figure 21B:
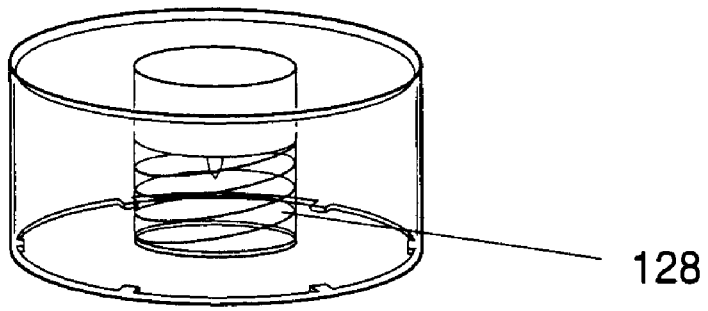
Figure 21C:
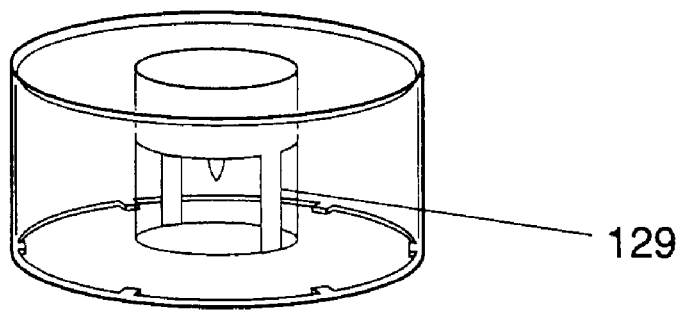

Depression of the cap 110 and convertor 100 also may be restricted by a collapsible shield 127 (as shown in FIG. 21a), a spring 128 (FIG. 21b), or breakable columns 129 (FIG. 21c). With each of these embodiments, force is required to advance the cap 110 and convertor 100.

Figure 22:
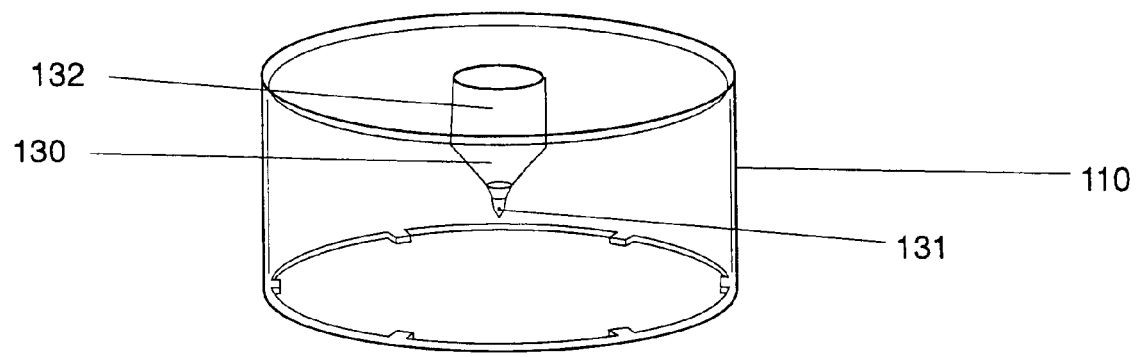
FIG. 22 shows an embodiment wherein the convertor is hollow and may remain in place to serve as a conduit for needle insertion or direct attachment of tubing or a syringe. The distal orifice may be recessed or at the tip.

It should be noted that, although the primary function of the convertor is to pierce the diaphragm in order to facilitate subsequent puncture by an inventive needle or cannula, in certain settings it might be preferable for the convertor to remain in the diaphragm and serve as a conduit. An embodiment of this mechanism is illustrated in FIG. 22, where the convertor 130 has a channel within the shaft which ends in an orifice 131 at or near the distal tip and has a hub 132 designed for fluidic engagement with a syringe or tubing at the convertor's proximal end.

Figure 23A:
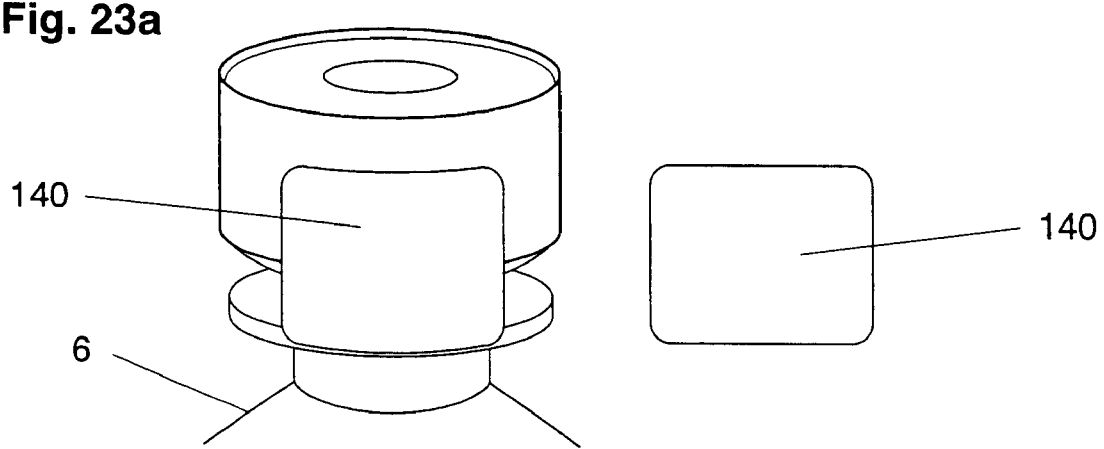
FIGS. 23a–23b show embodiments of the present invention wherein the convertor is incorporated into a cap which has been modified so that the integrity of the closure can be confirmed as by a tag (FIG. 23a) or a breakable circumferential seal (FIG. 23b) which remains intact until the cap is advanced.
Figure 23B:
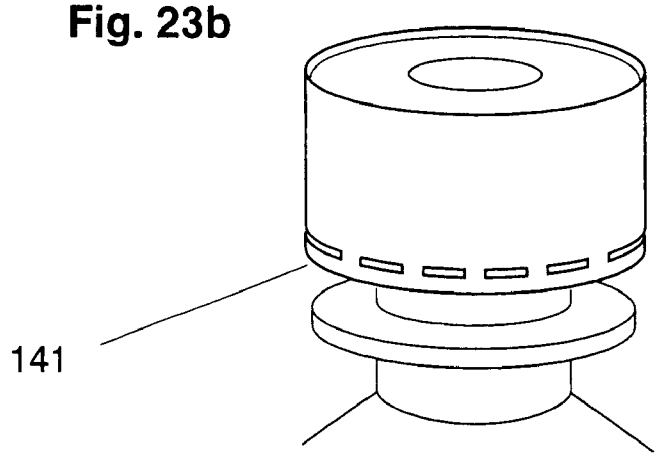

Since it is important to know when the convertor has been advanced and the diaphragm has been pierced, the maintenance of persistent closure should be readily confirmable. FIG. 23 shows examples of devices to ensure identification that a cap has been advanced and hence that the convertor may have penetrated the underlying diaphragm. FIG. 23a shows a tag 140 (as on an unopened liquor bottle). FIG. 23b shows a perforated or serrated seal 141 which extends circumferentially around the interface of the cap and diaphragm; said seal is torn upon turning the cap. The seal or tag may be made of any number of materials ranging from paper to metal. It would be broken upon turning the cap. Alternative means include shrink-wrap as on an unopened bottle (not shown).

Figure 24A:
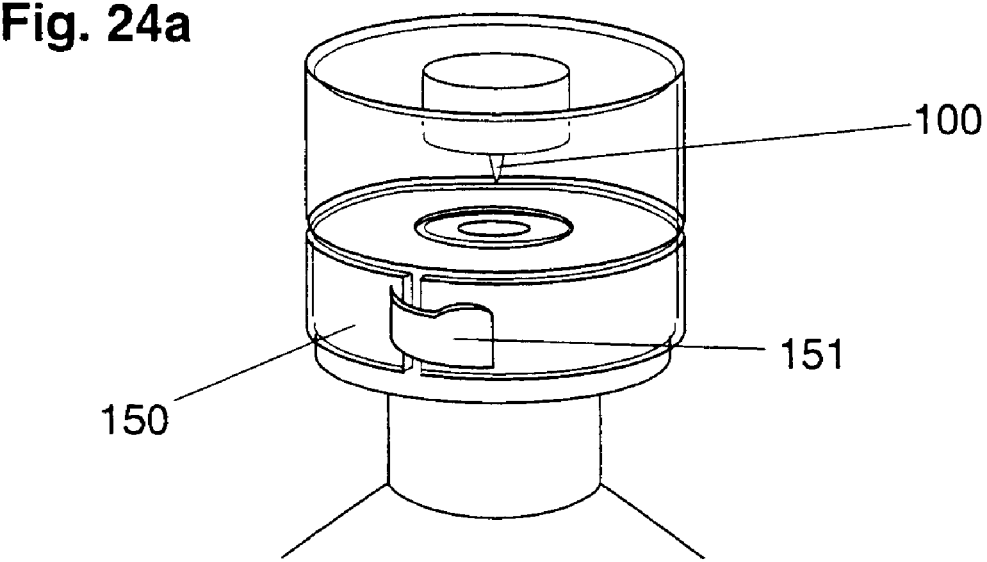
FIGS. 24a–24b show removable bands that lie at the lower border of the cap and prevent cap and convertor depression as well as their removal until the band is removed.
Figure 24B:
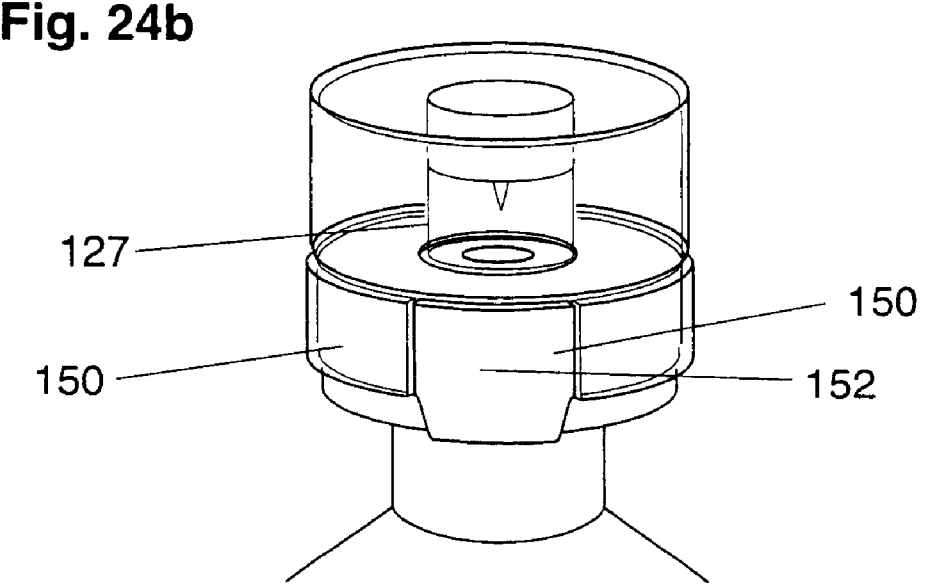

FIGS. 24a–24b illustrate other externally applied devices that both limit cap depression and identify when significant cap movement has occurred. In the illustrated embodiments of this mechanism, the lower portion of the cap has a readily removable band 150. This can be removed simply by pulling the horizontal tab 151 (FIG. 24a) or the vertical tab 152 (FIG. 24b), as would be performed to remove the top from a can of whipped cream. However, instead of simply removing the cap, one first can push it down to achieve penetration of (and hence conversion of) the diaphragm. FIG. 24b illustrates that these banded embodiments can function in combination with other mechanisms designed to prevent inadvertent diaphragm puncture (as previously shown in FIGS. 18–21). In the illustrated embodiment, the convertor is supported by a collapsible shield 127.

Figure 25A:
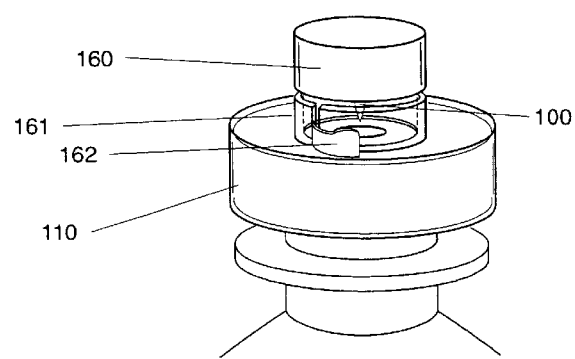
FIGS. 25a–25b show embodiments of the present invention wherein the convertor is incorporated into a bottle cap which has been modified so that only the central portion containing the convertor (as opposed to the entire cap) can be depressed to accomplish piercing of the underlying diaphragm. The convertor is advanced through the cap and diaphragm as a result of downward pressure by the user (analogous to, but different from, the mechanism involved with many sports-drink bottles).
Figure 25B:
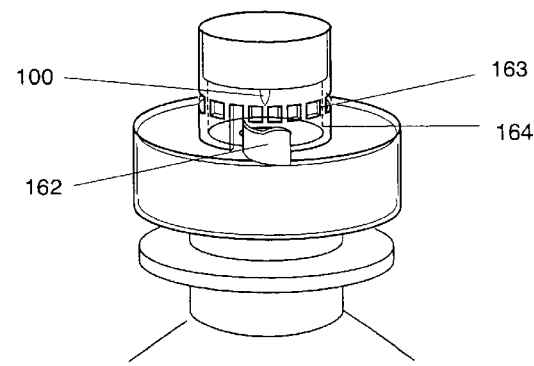

In several of the embodiments of the present invention, the convertor may be advanced independently of the remainder of the cap. Specifically, the convertor may be advanced through the cap and diaphragm as a result of downward pressure on the convertor housing 160. FIGS. 25a and 25b show how the convertor 100 may be maintained in the raised position by a removable band 161 which is adherent to the lower portion of the convertor housing 160 and/or to the base of the cap 110. Removal of the band is achieved by pulling a tab 162. Such removal may be facilitated by a perforated or serrated connection 163. The dotted line 164 shows the outline of a channel which may direct depression of the convertor 100. Following band removal, the convertor 100 may drop downward. Piercing of the diaphragm can be ensured by pressing down on the convertor 100 housing. Although not shown for the present embodiments, passive puncture of the diaphragm (i.e., without deliberate downward pressure) may be prevented by means such as breakable support columns, compressible shields and springs (as illustrated in FIG. 21) or by requiring that one provide sufficient downward pressure to overcome raised (ribbed) portions (analogous to the means used to open and close the nipple of many sports drink bottles) and/or deliberate twisting motion as shown for the entire cap in FIGS. 18–20.

Needles

Each of the needles of the present invention is designed to meet the following criteria: a) puncture but not tear the matched diaphragm(s); b) have a lesser likelihood of transmitting inoculum by inadvertent skin puncture as a consequence of having less likelihood of puncturing the skin than a standard hypodermic needle and/or less likelihood of exposing the victim of such a puncture to the inoculum within the hollow bore of the needle; c) allow for the use of a diaphragm with greater sealing and/or resealing properties than the preslit or preweakened diaphragm of currently described needleless systems.

As for standard hypodermic needles, the long axis of each of the inventive needles contains a hollow tubular channel (or through-bore) extending from the proximal hub end (which is structured for standard fluidic communication with other devices such as a syringe or infusion tubing) to one or more orifices located at the distal end. The orifice may be located at the end of taper. This so-called open-bevel design of the inventive series is tapered such that it is less sharp than a standard "penetrating but dangerous" needle.

Figure 26A:
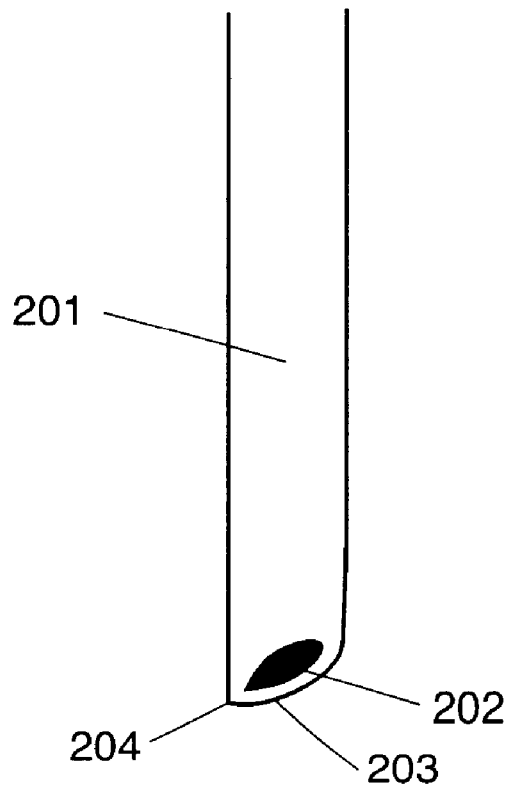
FIGS. 26a–26b are examples of the approximate range of tapers and tips that is characteristic of the open-tipped embodiments of the inventive series of inventive needles: a) open tapered tip of approximately 30°; b) open tapered tip of approximately 15–20°.
Figure 26B:
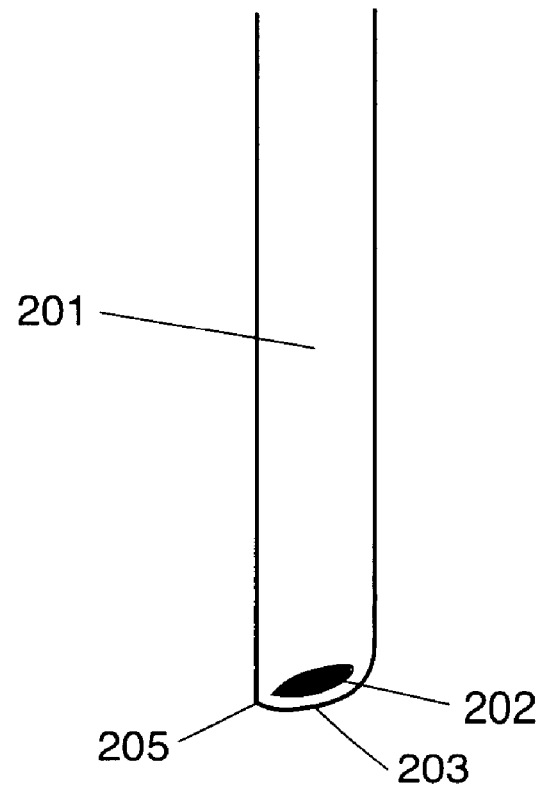

FIGS. 26a and 26b show open-beveled tapered needles with a shaft 201, a tubular channel which ends in an opening 202 at the tip 203. The tip 203 may define any of several different angles to the plane which is perpendicular to the longitudinal axis of the needle, including the approximately 35° angle 204 (FIG. 26a) and the approximately 20° angle 205 (FIG. 26b).

In most of the embodiments, the orifice(s) is near, but not at, the actual tip. We believe that healthcare worker safety may be achieved more efficiently with the closed-tip design. The recessed orifices may be located at various distances from the needle tip. The hub may be marked to delineate orifice orientation. The channel may be midline or offset. The shaft may be thick-walled or thin-walled. The taper may be symmetrical or biased.

Figure 27A:
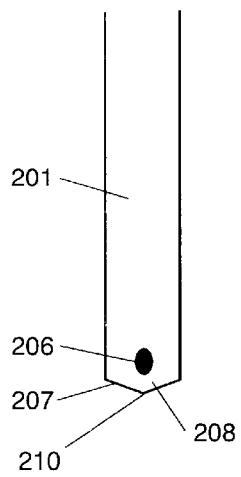
FIGS. 27a–27d are examples of the approximate range of tapers and tips that are characteristic of the closed-tipped embodiments of the inventive series: a) closed tapered tip of approximately 45°; b) closed tapered tip of approximately 20°; c) closed tapered tip with a rounded distal end; d) closed tapered tip with a flat distal end.
Figure 27B:
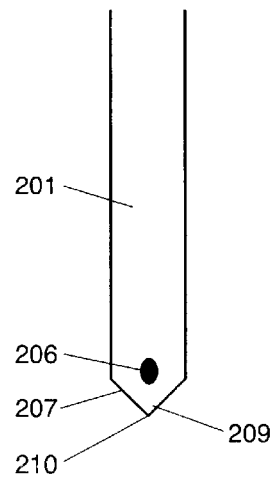
Figure 27C:
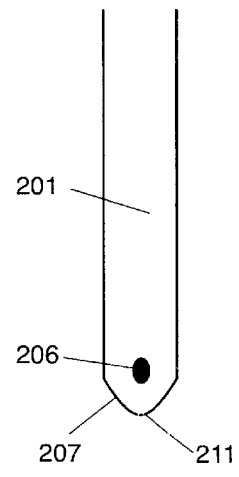
Figure 27D:
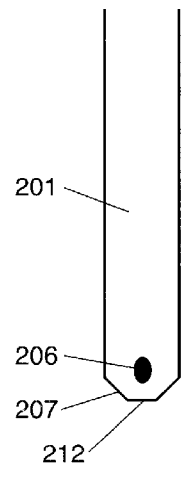

As illustrated in FIGS. 27a–27d, embodiments of the closed tip designs with recessed orifices 206 can have tips with tapers 207 ranging from approximately 15° (208 in FIG. 27a) to approximately 45° (209 in FIG. 27b). They may end in a pointed 210, rounded 211, or flat 212 distal end.

Figure 28:
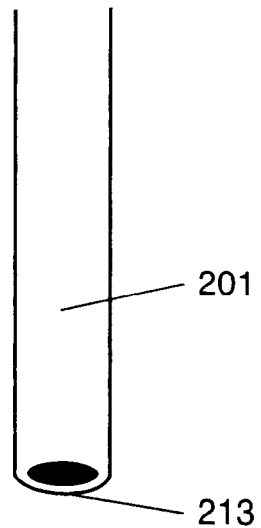
FIG. 28 shows an "absolutely" blunt cannula, consistent with that shown for needleless systems in the prior art.

Each of the tapered inventive needles can penetrate more readily than an absolutely blunt cannula (FIG. 28), whose end 213 is essentially without a taper.

Figure 29A:
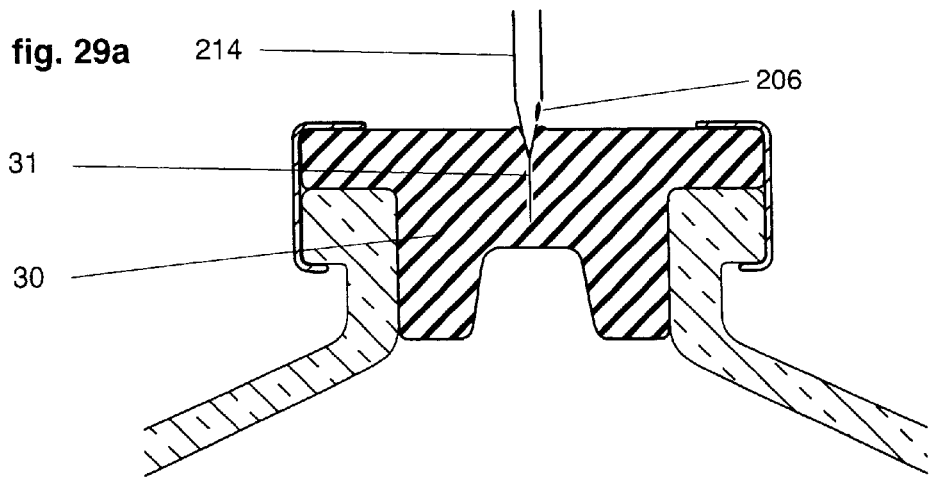
FIGS. 29a–29c show combinations of a preferred embodiment of an inventive needle with a matched diaphragm which has undergone prechannelling and/or preweakening prior to needle insertion: a) diaphragm with a slit; b) diaphragm with a preweakened region; c) diaphragm with a preweakened region and a slit (as may be created by insertion of a convertor).
Figure 29B:
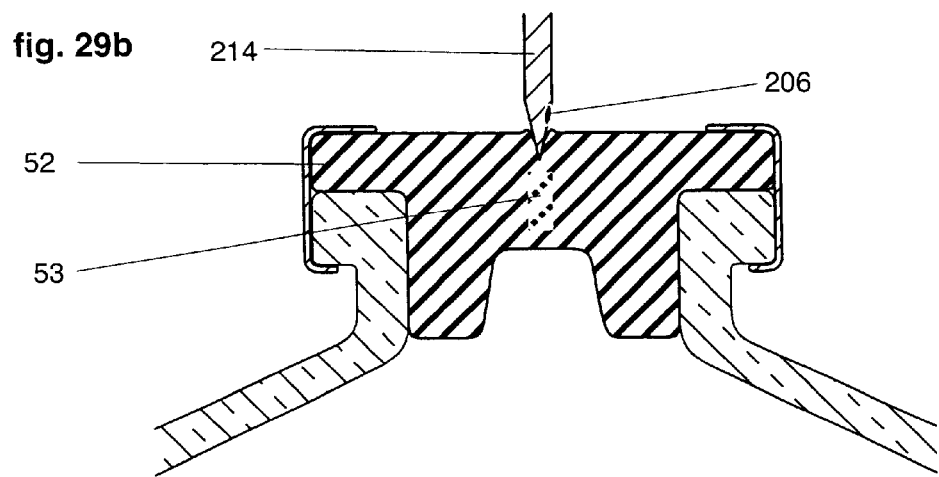
Figure 29C:
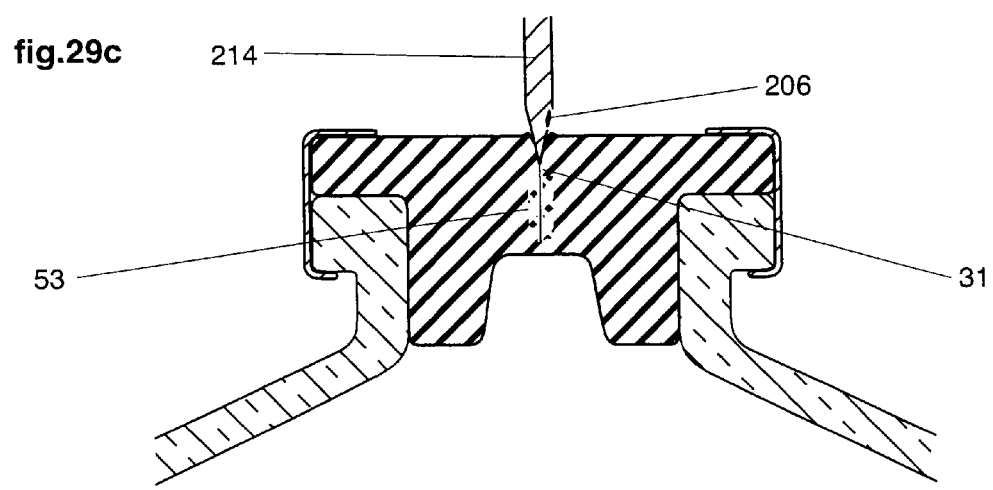

FIGS. 29a–29c show examples of an inventive needle 214 piercing an inventive (matched) diaphragm. FIG. 29a shows the process of inserting an inventive needle 214 with a recessed orifice 206 into an inventive diaphragm 30 with a channel 29 that was made either at the time of manufacture or by penetration with a convertor. FIG. 29b shows a comparable process in an inventive diaphragm 52 with a partially weakened region 53. FIG. 29c shows a comparable process in an inventive diaphragm with a partially weakened region 53 and a channel 31 above the preweakened region.

Also usable are needles covered with sheathes or caps as disclosed in Disclosure #1 and U.S. Pat. No. 5,478,328, both incorporated by reference.

Testing of Needles, Diaphragms and Their Combinations

Our goal is to use an inherently safe needle in combination with a diaphragm so long as the needle/diaphragm combination allows the desired degree of diaphragm integrity, efficient penetration, secure engagement, and resealability. Data to be collected include the following.

A. Diaphragm Effectiveness

1) Bacterial counts of fluids stored under seemingly sterile conditions in containers covered by the diaphragms under study before, during and after convertor and/or needle insertion. This can be determined for the anticipated duration of clinical use. For example, an intravenous line with injection ports typically is replaced every 48 hours; a single-use drug bottle should be discarded within minutes to hours, while a multi-use vial contains a preservative and should be discarded within 30 days after first use.

Figure 30:
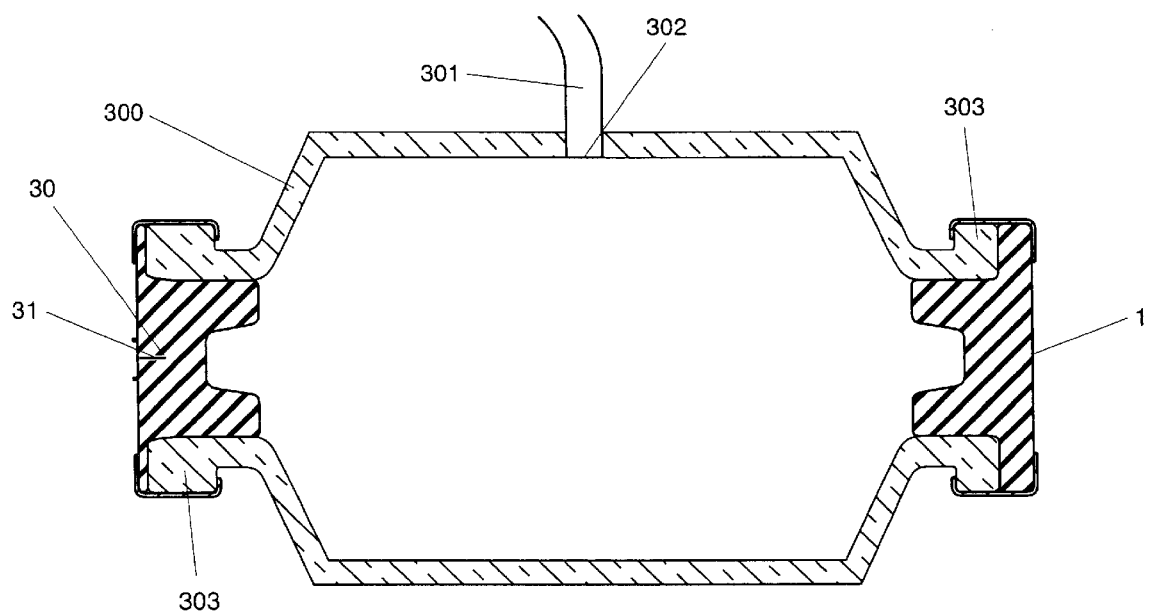
FIG. 30 shows an example of an arrangement to simultaneously test and compare two or more diaphragms with respect to their leak-free integrity in the face of different pressures. The internal pressures may be increased by infusing fluid through a separate port.

2) Integrity of the diaphragm in comparative studies. FIG. 30 shows a setup for comparing the ability of two or more diaphragms to resist leaking under identical conditions while fluid is delivered via tubing 301 or a syringe through a sealed orifice 302 over the range of temperatures, rates, pressures, and infusate consistencies that may be encountered during actual use. In the example, there are two diaphragm testing sites 303; an inventive diaphragm 30 with channel 31 is being compared to standard diaphragm 1. Additionally, the diaphragm can be compared during and after needle insertion(s). The inventive series of diaphragms will have integrity scores that exceed those of the needleless systems of the prior art since we are not limited to diaphragms which are penetrable by blunt cannulae from the time of manufacture (as described in the prior art). Likewise, the inventive systems will provide more secure engagement than blunt cannula needleless systems without supplemental means of securement. Whereas the prior art has not taught the use of needleless systems for covering openings wider than those covered by the diaphragms atop intravenous injection ports, an aforementioned advantage of the present invention is to enable use of a wider range of diaphragm sizes as may be required to cover openings atop wide-mouthed bottles. Their integrity can be tested by modifying the size of the openings 303 in the set-up illustrated in FIG. 30.

B. Needle Safety

1) Forces required for penetration of skin vs. diaphragm. A major objective of the design and testing processes of the present investigation is to increase healthcare worker safety by designing needle/diaphragm combinations which, upon testing and subsequent clinical use, demonstrate a high diaphragm/skin penetrability ratio. The goal is to design systems where the force required to pierce the diaphragm (typically in the range of 2 to 5 lbs but desirably less in certain embodiments) should be decidedly less than that required to pierce the skin.

2) We are introducing devices to test the relative penetrabilities.

Figure 31A:
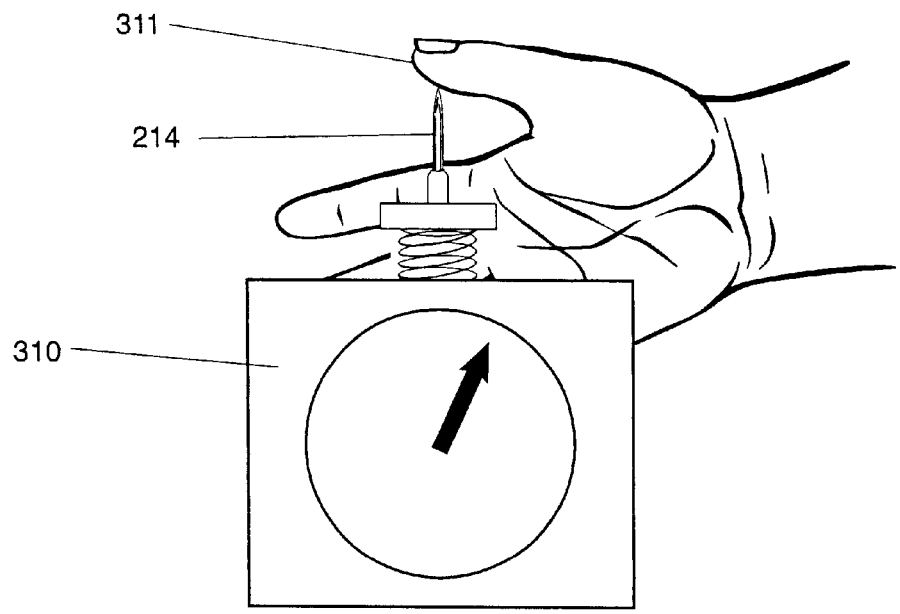
FIGS. 31a and 31b illustrate a device for determining the force required for a given needle to penetrate the skin (FIG. 31a) or a diaphragm (FIG. 31b) wherein the needle is mounted on a scale which records the force required for penetration.
Figure 31B:
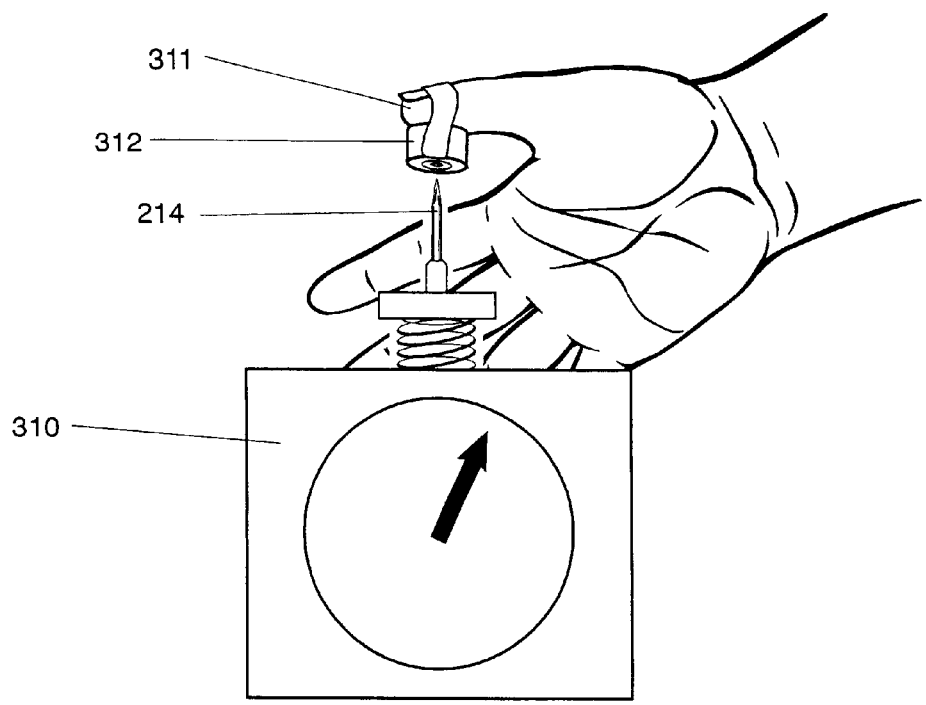

One such device is shown in FIGS. 31a and 31b. A needle 214 is attached to a scale 310 such that the tip of the needle 214 is pointed outward so as to measure the force required to pierce (or penetrate to a specific depth) skin as of the thumb 311 (FIG. 31a) or a diaphragm 312; said diaphragm may be supported independently or attached to the thumb (as shown in FIG. 31b).

Figure 32A:
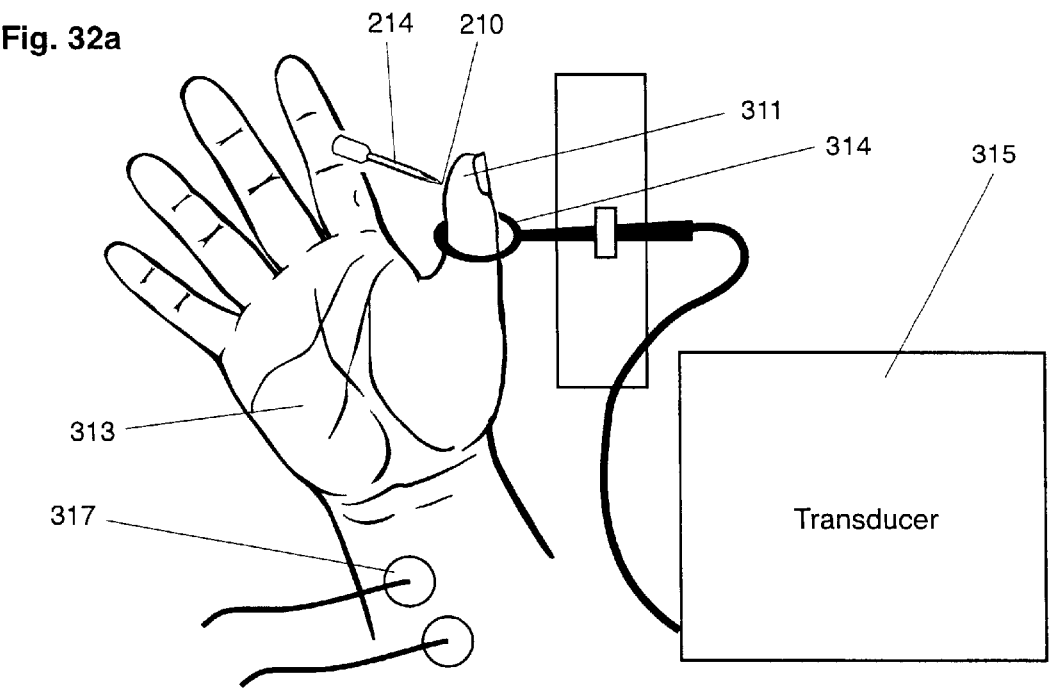
FIGS. 32a and 32b illustrate a more elaborate means of testing the penetrability of skin and diaphragms. The illustrated mechanism is designed to provide involuntary movements of the thumb by contraction of the adductor pollicis muscle as a result of stimulation of the ulnar nerve (analogous to the means used to assess neuromuscular weakness in patients undergoing general anesthesia). The force of contraction is recorded by a transducer (specifically an adductor pollicis force transducer). In the pictured embodiments, the needle is maintained in a fixed position in front of the thumb. In alternative embodiments, the needle can be secured to a thumb while the object to be punctured is maintained in a fixed position in front of it.
Figure 32B:
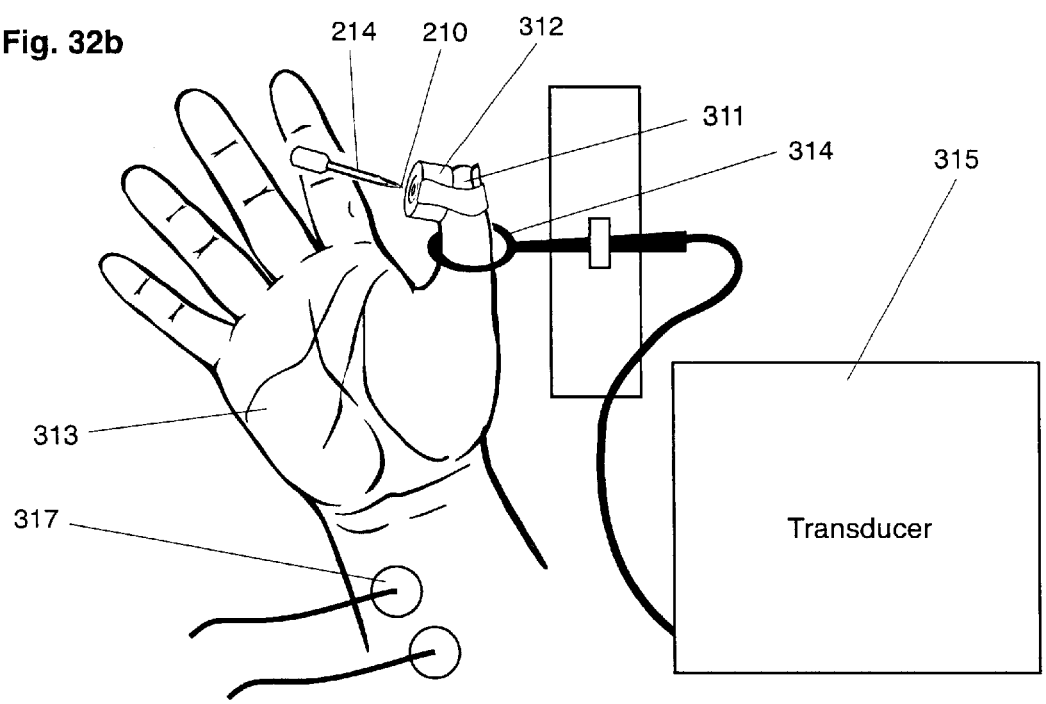

A more elaborate means of testing is illustrated in FIG. 32. A user's hand 313 is placed palm-side up under a strap (not shown) which limits the movement of all fingers except the thumb 311. The thumb 311 is then secured by a restraining device, such as a ring 314, which is attached to a pressure transducer 315 which measures the force of subsequent thumb movement. The needle 214 being tested is secured perpendicular to the thumb 311, with the needle point 210 touching or almost touching the palmar surface of the thumb 311 (FIG. 32a) or a diaphragm 312 attached to the thumb 311 (in FIG. 32b). (Alternatively, the needle 214 can be attached to the thumb so as to puncture items placed in front of the thumb—not shown.) The thumb 311 may be advanced voluntarily. However, it is more reliable to induce a standardized forward thumb movement with a nerve stimulator whose stimulating electrodes 317 are placed over the ulnar nerve. The stimulating current causes thumb adduction by inducing contraction of the adductor pollicis muscle. The degree of contraction depends on the number of contracting fibers, which in turn is dependent on the stimulating current. The stimulating current can be increased in 1–2 milliampere increments, while the resultant force of contraction is recorded.

The standard stimulus used to elicit nerve firing in the assessment of neuromuscular function in the clinical setting (0.2 milliseconds in duration repeated at a rate of 0.1 Hz=once every 10 seconds) was used for our initial trial. It reliably induces movement consistent with that which is associated with accidental self-puncture. Stimuli of different duration and/or repetitive stimuli may be utilized. Preload may be added, as indicated, to alter the amount of thumb movement. Even greater reliability may be achieved in anesthetized subjects (who will not resist thumb advancement).

During testing with the setup illustrated in FIG. 32, we found that a standard open-bevel needle consistently punctured the skin such that blood appeared (and pain was felt) at 9–10 mm Hg pressure. (Lesser forces, due to lower currents, did not cause skin puncture.) In contrast, a sharp closed tip needle required a pressure of >15 mmHg to puncture the skin (and this was to a depth which did not advance the orifice into the skin).

Needles and diaphragms designed in accordance with the present invention or for comparable purposes in other contexts can be tested and rated according to the present disclosure. Such ratings may include, but are not necessarily limited to, absolute force requirements for causing puncture of skin or diaphragm, as well as relative force requirements for piercing skin vs. diaphragm. The forces required for penetration to a depth that allows a needle's orifices to be advanced through the skin (and thus deliver an infectious inoculum) may be determined in a variety of ways, including recording the aforementioned penetrability studies on film.

Statistical data will include mean, median, standard deviation, standard error, as well as the confidence intervals, and coefficients of repeatability and variation. Embodiments of the inventive serves will be compared to the Strong Diaphragm/Dangerous Needle and Weak Diaphragm/Safe Cannula combinations of the prior art. Ideally, the force required to puncture the skin should be many times greater than (at least double) that required to penetrate a matched diaphragm. Needles also may be rated according to their incidence of skin puncture in clinical settings. Parametric data will be analyzed by paired t-testing and analysis of variance with appropriate modifications for multiple comparisons. Non-parametric data may be assessed using ranking techniques. Incidence (e.g. of skin penetration among different needles in different contexts) may be compared using Chi-squared analysis.

The relative simplicity of the aforementioned means of testing enables rapid testing of a wide range of needles, diaphragms, and convertors. If deemed indicated, one can utilize the teaching of the prior art to guide initial testing. For example, for a needle with a diameter of 0.10 inch (0.254 cm), we will begin testing with a slit of the diameter recommended for absolutely blunt cannula in the prior art. The greater sharpness of the inventive needles will allow progressive decrease of the relative size of the slit to attain increased diaphragm integrity while seeking to ensure healthcare worker safety.

Thus, this disclosure teaches a combined testing procedure which addresses both testing of diaphragm integrity and penetrability as well as relative needle safety using combined indices, in the design and testing of needle/diaphragm configurations.

What is claimed is:

1. A method for containing, administering, infusing, injecting, or withdrawing a material before or after a clinical use, said method comprising the steps of:

prior to clinical use, providing a vessel which is sealed by an elastically deformable diaphragm which provides a clinically acceptable shelf-life for said vessel;

at the time of clinical use, employing a converter which is operable for making a puncture hole in said elastically deformable diaphragm to convert the diaphragm into a more readily penetrable diaphragm; and inserting a fluid conduit into said elastically deformable diaphragm, said fluid conduit being insertable into said diaphragm only after said puncture hole is made by said converter.

2. The method of claim 1, wherein, prior to conversion, the diaphragm is penetrable only by a relatively sharp needle and after conversion, the diaphragm is penetrable by a needle less sharp than the relatively sharp needle.

3. The method of claim 2, wherein the diaphragm is partially compromised.

4. The method of claim 3, wherein, prior to conversion, the diaphragm has a small or incomplete slit or series of slits.

5. The method of claim 3, wherein, prior to conversion, the diaphragm has a small or incomplete hole.

6. The method of claim 3, wherein, prior to conversion, the diaphragm has undergone partial weakening.

7. The method of claim 1, wherein, prior to conversion, the diaphragm is penetrable only by a relatively sharp needle and after conversion, the diaphragm is penetrable by a blunt cannula.

8. The method of claim 7, wherein, the diaphragm is partially compromised.

9. The method of claim 8, wherein, prior to conversion, the diaphragm has a small or incomplete slit or series of slits.

10. The method of claim 8, wherein prior to conversion, the diaphragm has a small or incomplete hole.

11. The method of claim 8, wherein, prior to conversion, the diaphragm has undergone partial weakening.

12. The method of claim 1, wherein the convertor is a component of a cap which fits atop the diaphragm.

13. The method of claim 12, wherein a safety mechanism is attached to the converter to prevent inadvertent penetration of the diaphragm by the converter.

14. The method of claim 12, wherein the convertor has a channel and orifice.

15. The method of claim 12, further comprising employing a device for identifying when the convertor has been advanced and thus may have penetrated the diaphragm.

16. The method of claim 12, wherein the convertor is advanced upon the diaphragm by downward displacement of the entire cap.

17. The method of claim 12, wherein the converter is advanced upon the diaphragm solely by downward displacement of a region of the cap which houses the convertor.

18. The method of claim 12, wherein said cap comprises a structure which guides said cap to a predetermined position with respect to the diaphragm.

19. The method of claim 1, wherein said converter comprises a point which is generally rounded in its outer shape for making said puncture hole.

20. The method of claim 1, wherein said converter further comprises a handle.

21. The method of claim 1, wherein said fluid conduit comprises a needle with a point.

22. The method of claim 21, wherein said needle point is closed and said needle has a recessed fluid-receiving orifice at a distal end thereof.

23. The method of claim 22, wherein said needle point defines in cross-section a pair of opposite sides which define substantially a 90° angle with respect to each other.

24. The method of claim 21, wherein said needle point is closed and defines in cross-section a pair of opposite sides which define substantially a 90° angle with respect to each other.

25. The method of claim 1, wherein said puncture hole formed by said converter has a rounded shape.

26. A method for converting a diaphragm and transferring a fluid, said fluid having a predetermined clinically acceptable shelf-life, said method using a needle which is provided with a proximal hub and distal orifice, wherein fluidic communication occurs inside the needle between the proximal hub and the distal orifice; said method comprising the steps of:

prior to clinical use, holding said fluid in a vessel which is capable of sealing said fluid therein by an elastically deformable diaphragm which provides said clinically acceptable shelf-life for said fluid in said vessel, wherein said deformable diaphragm provides a leak-free closure and is not readily penetrable by said needle prior to clinical use; and at the time of clinical use, employing a converter for penetrating the diaphragm and forming a puncture hole in the diaphragm, wherein after the converter penetrates the diaphragm, the diaphragm is readily penetrable by the needle.

27. The method of claim 26, wherein the needle is a blunt cannula.

28. The method of claim 26, wherein the needle has an angled open tip that is less than approximately 45° to the longitudinal axis of the needle.

29. The method of claim 26, wherein the needle has a blunted tip.

30. The method of claim 26, wherein the needle has a closed tip with an orifice that is recessed from the tip.

31. The method of claim 26, wherein the converter is a component of a cap which fits atop the diaphragm.

32. The method of claim 31, wherein said cap comprises a structure which guides said cap to a predetermined position with respect to the diaphragm.

33. The method of claim 26, wherein said needle has a closed point and said distal orifice is recessed from said point.

34. The method of claim 33, wherein said needle point defines in cross-section a pair of opposite sides which define substantially a 90° angle with respect to each other.

35. The method of claim 26, wherein said converter comprises a point which is generally rounded in its outer shape for making said puncture hole.

36. A system for containing, administering, infusing, injecting, or withdrawing a material before or after a clinical use, comprising:

a vessel having a predetermined clinically acceptable shelf-life;

said vessel being sealed by an elastically deformable diaphragm which provides said clinically acceptable shelf-life for said vessel;

a converter which is operable at the time of clinical use for making a puncture in said elastically deformable diaphragm to convert the diaphragm into a more readily penetrable diaphragm; and a fluid conduit which is insertable into said elastically deformable diaphragm after said puncture is made by said converter;

said fluid conduit comprising a needle with a blunt closed tip and a recessed fluid-receiving orifice.

37. The system of claim 36, wherein said needle tip defines in cross-section a pair of opposite sides which define substantially at least a 90° angle with respect to each other.

38. The system of claim 36, wherein, prior to conversion, the diaphragm is partially compromised.

39. The system of claim 38, wherein, prior to conversion, the diaphragm has a small incomplete slit or series of slits.

40. The system of claim 38, wherein, prior to conversion, the diaphragm has a small or incomplete hole.

41. The system of claim 38, wherein, prior to conversion, the diaphragm has undergone partial weakening.

42. The system of claim 36, wherein, prior to conversion, the diaphragm is intact.

43. The system of claim 36, wherein said converter comprises a point having a generally rounded outer shape for making said puncture.

44. A system for containing, administering, infusing, injecting, or withdrawing a material before or after a clinical use, comprising:
   a vessel having a predetermined clinically acceptable shelf-life;
   said vessel being sealed by an elastically deformable diaphragm which provides said clinically acceptable shelf-life for said vessel;
   a converter which is operable at the time of clinical use for making a puncture in said elastically deformable diaphragm to convert the diaphragm into a more readily penetrable diaphragm; and
   a fluid conduit which is insertable into said elastically deformable diaphragm after said puncture is made by said converter;
      wherein the converter is a component of a cap which is securable on said vessel atop said diaphragm.

45. The system of claim 44, wherein, prior to conversion, the diaphragm is not substantially penetrable by said fluid conduit, and after conversion, the diaphragm is substantially penetrable by said fluid conduit; and wherein said fluid conduit is a blunt cannula.

46. The system of claim 44, wherein, prior to conversion, the diaphragm is not substantially penetrable by said fluid conduit, and after conversion, the diaphragm is substantially penetrable by said fluid conduit; and wherein said fluid conduit comprises a needle with a closed tip and a recessed fluid-receiving orifice.

47. The system of claim 44, wherein, prior to conversion, the diaphragm is partially compromised.

48. The system of claim 44, wherein, prior to conversion, the diaphragm has a small or incomplete slit or series of slits.

49. The system of claim 44, wherein prior to conversion, the diaphragm has a small or incomplete hole.

50. The system of claim 44, wherein, prior to conversion, the diaphragm has undergone partial weakening.

51. The system of claim 44, wherein, prior to conversion, the diaphragm is intact.

52. The system of claim 44, further comprising a thread arrangement for engaging said cap and vessel.

53. The system of claim 52, further comprising a release which is operable to disengage the thread arrangement between the vessel and cap without unscrewing.

54. The system of claim 44, further comprising a safety mechanism attached to the converter to prevent inadvertent relative movement of the converter and the diaphragm.

55. The system of claim 44, wherein the converter has a channel which provides fluid communication between said vessel and an orifice in said cap.

56. The system of claim 44, further comprising a device which identifies when the converter has been advanced and thus may have penetrated the diaphragm.

57. The system of claim 56, wherein said device comprises a breakable seal.

58. The system of claim 44, wherein the converter is advanced upon the diaphragm by downward displacement of the entire cap.

59. The system of claim 44, wherein the converter is advanced upon the diaphragm by downward displacement of only a region of the cap which houses the converter.

* * * * *